US012760273B2

(12) United States Patent
Thomas et al.

(10) Patent No.: US 12,760,273 B2
(45) Date of Patent: Oct. 13, 2026

(54) NONVIRAL MODIFICATION OF T CELL GENE EXPRESSION

(71) Applicant: Global Life Sciences Solutions Canada ULC, Vancouver (CA)

(72) Inventors: Anitha Thomas, New Westminster (CA); Andrew William Brown, Vancouver (CA); Rebecca Anne Grace De Souza, Vancouver (CA); Tara Fernandez, Port Moody (CA)

(73) Assignee: GLOBAL LIFE SCIENCES SOLUTIONS CANADA ULC, Vancouver (CA)

( * ) Notice: Subject to any disclaimer, the term of this patent is extended or adjusted under 35 U.S.C. 154(b) by 1061 days.

(21) Appl. No.: 17/602,942

(22) PCT Filed: Apr. 14, 2020

(86) PCT No.: PCT/CA2020/050498
§ 371 (c)(1),
(2) Date: Oct. 11, 2021

(87) PCT Pub. No.: WO2020/210901
PCT Pub. Date: Oct. 22, 2020

(65) Prior Publication Data

US 2022/0162552 A1 May 26, 2022

Related U.S. Application Data

(60) Provisional application No. 62/923,525, filed on Oct. 19, 2019, provisional application No. 62/861,220, filed on Jun. 13, 2019, provisional application No. 62/833,993, filed on Apr. 15, 2019.

(51) Int. Cl.

| | |
|---|---|
| ***C12N 5/0783*** | (2010.01) |
| ***A61K 40/11*** | (2025.01) |
| ***A61K 40/31*** | (2025.01) |
| ***A61K 40/42*** | (2025.01) |
| ***C12N 15/88*** | (2006.01) |

(52) U.S. Cl.
CPC ............ *C12N 5/0636* (2013.01); *A61K 40/11* (2025.01); *A61K 40/31* (2025.01); *A61K 40/4211* (2025.01); *C12N 15/88* (2013.01); *C12N 2500/36* (2013.01); *C12N 2500/50* (2013.01); *C12N 2510/00* (2013.01)

(58) Field of Classification Search
CPC .. C12N 5/0636; C12N 15/88; A61K 39/4631; A61K 39/464412; A61K 39/4611
See application file for complete search history.

(56) References Cited

U.S. PATENT DOCUMENTS

| | | | |
|---|---|---|---|
| 5,753,613 | A | 5/1998 | Ansell et al. |
| 6,040,177 | A | 3/2000 | Riddell et al. |
| 6,306,388 | B1 | 10/2001 | Nair et al. |
| 6,734,171 | B1 | 5/2004 | Saravolac et al. |
| D771,834 | S | 11/2016 | Leaver et al. |
| D771,883 | S | 11/2016 | Leaver et al. |
| D772,427 | S | 11/2016 | Leaver et al. |
| 9,758,795 | B2 | 9/2017 | Cullis et al. |
| D800,335 | S | 10/2017 | Chang et al. |
| D800,336 | S | 10/2017 | Chang et al. |
| D803,416 | S | 11/2017 | Leaver et al. |
| D812,242 | S | 3/2018 | Chang et al. |
| 9,943,846 | B2 | 4/2018 | Cullis et al. |
| 10,076,730 | B2 | 9/2018 | Wild et al. |
| 10,143,758 | B2 | 12/2018 | Guild et al. |
| 10,159,652 | B2 | 12/2018 | Walsh et al. |
| 10,342,760 | B2 | 7/2019 | Ramsay et al. |
| 10,383,952 | B2 | 8/2019 | Payne et al. |
| 10,399,937 | B2 | 9/2019 | Payne et al. |
| 10,507,183 | B2 | 12/2019 | Guild et al. |
| 2004/0026223 | A1 | 2/2004 | Schmidt et al. |
| 2010/0309986 | A1 | 12/2010 | Fukisawa |
| 2011/0003380 | A1 | 1/2011 | Miltenyi et al. |
| 2012/0295832 | A1 | 11/2012 | Constien et al. |
| 2013/0323269 | A1 | 12/2013 | Manoharan et al. |
| 2014/0162170 | A1 | 6/2014 | Amemiya |
| 2016/0213777 | A1* | 7/2016 | Shoyele ................. C07K 16/00 |
| 2016/0235688 | A1 | 8/2016 | Walsh et al. |

(Continued)

FOREIGN PATENT DOCUMENTS

| | | | |
|---|---|---|---|
| CA | 3027201 | A1 | 12/2017 |
| CA | 3040337 | A1 | 5/2018 |

(Continued)

OTHER PUBLICATIONS

Siddiqui et al. International journal of pharmaceutics vol. 431, 1-2 (2012): 222-9. (Year: 2012).*
Yang Liu et al. Molecular therapy : the journal of the American Society of Gene Therapy vol. 18,4 (2010): 669-70. (Year: 2010).*
Kerwin BA. Polysorbates 20 and 80 used in the formulation of protein biotherapeutics: structure and degradation pathways. J Pharm Sci. 2008;97(8):2924-2935. doi:10.1002/jps.21190 (Year: 2008).*
Zukancic D, Suys EJA, Pilkington EH, Algarni A, Al-Wassiti H, Truong NP. The Importance of Poly(ethylene glycol) and Lipid Structure in Targeted Gene Delivery to Lymph Nodes by Lipid Nanoparticles. Pharmaceutics. 2020;12(11):1068. Published Nov. 9, 2020. doi:10.3390/pharmaceutics12111068 (Year: 2020).*

(Continued)

*Primary Examiner* — Maria G Leavitt
*Assistant Examiner* — Kodye Lee Abbott
(74) *Attorney, Agent, or Firm* — Lathrop GPM LLP; Malaika O.D. Tyson; Jason Kuchar

(57) ABSTRACT

There is provided a lipid mix composition comprising ionizable lipid, a structural lipid such as DSPC, a sterol, and a surfactant such as polysorbate 80, polyoxyethylene (10) stearyl ether, polyoxyethylene (20) stearyl ether, or D-α-Tocopherol polyethylene glycol 1000 succinate. The lipid mix compositions find particular use in transfecting difficult to transfect cells and maintaining the viability of those cells. The lipid mix compositions are particularly well suited to T cell transfection ex vivo.

11 Claims, 24 Drawing Sheets

(56) References Cited

U.S. PATENT DOCUMENTS

| | | | |
|---|---|---|---|
| 2018/0000953 | A1 | 1/2018 | Almarsson et al. |
| 2018/0093232 | A1 | 4/2018 | Wild et al. |
| 2018/0111830 | A1 | 4/2018 | Wild et al. |
| 2018/0333366 | A1 | 11/2018 | Benenato et al. |
| 2019/0292130 | A1 | 9/2019 | Peer et al. |
| 2020/0023358 | A1 | 1/2020 | Wild et al. |

FOREIGN PATENT DOCUMENTS

| | | | |
|---|---|---|---|
| CA | 3 089 117 | A1 | 8/2019 |
| WO | 2009096558 | A1 | 8/2009 |
| WO | 2010033140 | A3 | 3/2010 |
| WO | 2013014910 | A1 | 1/2013 |
| WO | 2014172045 | A1 | 10/2014 |
| WO | WO 2016/118724 | A1 | 7/2016 |
| WO | WO 2017/019935 | A1 | 2/2017 |
| WO | WO 2017/049074 | A1 | 3/2017 |
| WO | WO 2017/218704 | A1 | 12/2017 |
| WO | 2018064755 | A1 | 4/2018 |
| WO | 2018089540 | A1 | 5/2018 |
| WO | 2018119514 | A1 | 7/2018 |
| WO | 2018144775 | A1 | 8/2018 |
| WO | 2019152557 | A1 | 8/2019 |
| WO | 2020047061 | A1 | 3/2020 |

OTHER PUBLICATIONS

Japan Patent Office, Office Action issued in counterpart Japanese Patent Application No. 2021-560983, mailed on Nov. 29, 2022.

"HiPerFect Transfection Reagent Protocols and Troubleshooting for transfection of siRNA and miRNA into eukaryotic cell", corresponding to May 2008 of English edition, *QUIAGEN*, 50 pages (2010).

European Patent Office, Extended European Search Report issued in counterpart European Patent Application No. 20792066.1, mailed on Dec. 8, 2022.

Canadian Intellectual Property Office, Examiner's Report issued in counterpart Canadian Application No. 3,133,394, mailed on Nov. 9, 2022.

Fitzgerald, J. et al. "Cytokine Release Syndrome After Chimeric Antigen Receptor T Cell Therapy for Acute Lymphoblastic Leukemia" Crit Care Med, Feb. 2017, pp. e124-e131, vol. 45, No. 2.

Foster, J. et al. "Purification of mRNA Encoding Chimeric Antigen Receptor is Critical for Generation of a Robust T-Cell Response" Human Gene Therapy, 2018, pp. 1-11, vol. X No. X.

Frey, N. et al. "Cytokine Release Syndrome with Chimeric Antigen Receptor T Cell Therapy" Biology of Blood and Marrow Transplantation, 2019, pp. e123-e127, vol. 25.

Garg, S. et al. "Microfluidics: a transformational tool for nanomedicine development and production", Journal of Drug Targeting, 2016, pp. 821-835, vol. 24, No. 9.

Green, J. et al. "Coordinate Regulation of T Cell Activation by CD2 and CD28" J Immunol, 2000, pp. 3591-3595, vol. 164.

Iriguchi, S. et al. "Toward the Developments of tru "off-the-shelf" synthetic T-Cell immunotherapy", Cancer Science, 2019, pp. 16-22, vol. 110.

Jeffs, L. et al. "A Scalable, Extrusion-Free Method for Efficient Liposomal Encapsulation of Plasmid DNA", Pharmaceutical Research, 2005, pp. 362-372, vol. 22, No. 3.

Kebriaei, P. et al. "Phase I trials using Sleeping Beauty to generate CD19-specific CAR T cells" The Journal of Clinical Investigation, 2016, pp. 3363-3376, vol. 126, No. 9.

Klebanoff, C. et al. "Sorting through subsets: Which T cell populations mediate highly effective adaptive Immunotherapy?" J Immunother., 2012, pp. 651-660, vol. 35, No. 9.

Monjezi, R. et al. "Enhanced CAR T-Cell engineering using non-viral Sleeping Beauty transposition from minicircle vectors" Leukemia, 2017, pp. 186-194, vol. 31.

Nianias, A. et al. "Induced Pluripotent Stem Cell (iPSC)-Derived Lymphocytes for Adoptive Cell Immunotherapy: Recent Advances and Challenges" Current Hematologic Malignancy Reports, 2019, pp. 261-268, vol. 14.

Obstfeld, A. et al. "Cytokine release syndrome associated with chimeric-antigen receptor T-cell therapy: clinicopathological insights" Blood, 2017, pp. 2569-2572, vol. 130, No. 23.

Patel, S. et al. "Naturally occurring cholesterol analogues in lipid nanoparticles induce polymorphic shape and enhance intracellular deliver of mRNA" Nature Communications, 2020, pp. 1-13, Volume.

Porter, D. et al. "Chimeric antigen receptor T cells persist and induce sustained remissions in relapsed refractory chronic lyphocytic leukemia", Sci Transl Med., 2015, pp. 1-25, vol. 7, No. 303.

Riley, R. et al. "Delivery technologies for cancer immunotherapy", Nature Reviews, 2019, pp. 175-196, vol. 18.

Smith, T. et al. "In situ programming of leukaemia-specific T cells using synthetic DNA nanocarriers" Nay Nanotechnol, 2017, pp. 813-820, vol. 12, No. 8.

Stroock, A. et al. "Chaotic Mixer for Microchannels", Science, 2002, pp. 647-651, vol. 295.

Svoboda, J. et al. "Nonviral RNA chimeric antigen receptor-modified T cells in patients with Hodgkin lymphoma", Blood, 2018, pp. 1022-1026, vol. 132, No. 10.

Terakura, S. et al. "Generation of CD19-chimeric antigen receptor modified CD8+ T cells derived from virus specific central memory T cells" Blood, 2012, pp. 72-82, vol. 119, No. 1.

Vairy, S. et al. "CTL019 (tisagenlecleucel): CAR-T therapy for relapsed and refractory B-Cell acute lymphoblastic leukemia" Drug Design, Development and Therapy, 2018, pp. 3885-3898, vol. 12.

Veiga, N. et al. "Cell Specific delivery of modified mRNA expressing therapeutic proteins to leukocytes", Nature Communications, 2018, pp. 1-9, vol. 9.

Wang, X. et al. "Phenotypic and Functional Attributes of Lentivirus Modified CD19-specific Human CD8+ Central Memory T Cells Manufactored at Clinical Scale", J Immunother, 2012, pp. 689-701, vol. 35, No. 9.

Zhang, S, et al. "Preparation of solid lipid nanoparticles in co-flowing microchannels", Chemical Engineering Journal, 2008, pp. 324-328, vol. 144.

* cited by examiner

A

B pcDNA3.1-anti-CD19-h(BBζ)-EGFP-2nd-CAR(T7 Mut)
7649 bp

NONVIRAL MODIFICATION OF T CELL GENE EXPRESSION

CROSS-REFERENCE TO RELATED APPLICATIONS

This application takes priority from U.S. Provisional Applications 62/833,993 filed Apr. 15, 2019; 62/861,220 filed Jun. 13, 2019; and 62/923,525 filed Oct. 19, 2019.

BACKGROUND

(a) Field

The subject matter disclosed generally relates to delivery of nucleic acid to living cells, specifically living T lymphocytes (T cells), while maintaining their viability.

(b) Related Prior Art

Altering gene expression for therapeutic purposes can be achieved by delivering nucleic acids in lipid nanoparticles (LNPs) to cells. Exogenous mRNA has promise as a means of generating in vivo protein expression, and when delivered by LNP rather than viral vectors, avoids the side effects and safety issues that viral delivery effects.

Chimeric Antigen Receptor T cell therapy (CAR) is a type of targeted immunotherapy now approved for human use (Kymriah™ tisagenlecleucel and Yescarta™ axicabtagene ciloleucel). The process uses cells from the subject being treated, selects and enriches for T cells, and then engineers these cells using a viral vector to express a chimeric antigen receptor (CAR). The cells are returned to the subject, resulting in immunotherapy. [1]

Despite the success of CAR treatment, there are issues: a) not all the treated T cells have CAR, b) there is variability in the amount of CARs expressed on the T cells that are transfected, c) patients undergoing CAR have often had multiple rounds of chemotherapy which means less healthy T cells which are harder to enrich, and 4) there is a high incidence (46% or more) in patients of Cytokine Release Syndrome (CRS). [2, 3] Patients with CRS require intensive care unit level care, and treatment with powerful and expensive immunotherapies such as tocilizumab (Actemra™).

Viral based to T-cell transformation have been tried, but are labor intensive, expensive and pose manufacturing and regulatory challenges. Vector design and development takes time as suitable vectors determine the efficiency of transduction. Also, virus manufacturing methods are expensive because they are highly regulated, need a lot of equipment, and labor intensive (one batch for each patient).

Viral based transfection also poses the risk that viral genome may randomly insert into the human genome, and requires that the patient leave the hospital to have T cells harvested and treated at a specialized viral manufacturing facility.

Another T cell transformation technology uses electroporation and circular DNA to revise T cell protein expression. Electroporated cells, however, can take a long time to proliferate, a sign indicating that health of the T cells have been affected by the process. A recent study showed that the viability of T Cells after electroporation was 31% as opposed to LNP mediated mRNA delivery.[1] The "Sleeping Beauty CART Therapy" is such an electroporation modality, but was put on hold in 2018.[4, 5]

A nonviral approach that is less destructive than electroporation would advance T cell mediated immunotherapy treatments, while preserving T cell viability and subject health.

SUMMARY OF THE INVENTION

According to an embodiment, there is provided a lipid mix composition including 35-55 Mol % ionizable lipid, 5-25 Mol % structural lipid, 25-40 Mol % sterol, and 0.1-3 Mol % surfactant. According to another embodiment, the composition is mixed with a nucleic acid to form lipid particles. According to another embodiment, there is provided a lipid mix composition for use in transfecting nucleic acid into target cells. According to another embodiment, there is provided a lipid mix composition in which said transfecting takes place ex vivo.

According to another embodiment, there is provided a lipid mix in which the structural lipid is DSPC. In another embodiment, the DSPC is present at 10-20 Mol %. In yet another embodiment, the DSPC is present at 20 Mol %. In another embodiment, there is provided a lipid mix in which the surfactant is Polyoxyethylene (10) stearyl ether. According to another embodiment, there is provided a lipid mix in which the surfactant is polysorbate 80. In another embodiment the surfactant is polyoxyethylene (40) stearate. In another embodiment, the surfactant is D-α-Tocopherol polyethylene glycol 1000 succinate.

In embodiments of the invention, the ionizable lipid is any ionizable lipid. In some embodiments, the ionizable lipid is BOCHD-C3-DMA. In embodiments of the invention, the ionizable lipid is Dlin-MC3-DMA. In embodiments of the invention, the ionizable lipid is DODMA. In embodiments of the invention, the ionizable lipid is KC2 (Dlin-KC2-DMA). In other embodiments, the ionizable lipid is C12-200.

In embodiments of the invention, the ionizable lipid is from 40-50 Mol %, the structural lipid is from 10-20 Mol % DSPC, the sterol is from 37-39 Mol %, and the surfactant is from 1-3 Mol %.

In further embodiments of the invention, the ionizable lipid comprises 50 Mol %, the structural lipid comprises 10 Mol % DSPC, the sterol comprises 37.5 Mol % cholesterol, and the surfactant comprises 2.5 Mol % polyoxyethylene (10) stearyl ether.

In other embodiments, the ionizable lipid comprises 40 Mol %, the structural lipid comprises 20 Mol % DSPC, the sterol comprises 37.5 Mol % cholesterol, and the surfactant comprises 2.5 Mol % polyoxyethylene (10) stearyl ether.

In yet other embodiments of the invention, a lipid mix composition is disclosed wherein the ionizable lipid comprises 40 Mol %, the structural lipid comprises 20 Mol % DSPC, the sterol comprises 38.5 Mol % cholesterol, and the surfactant comprises 1.5 Mol % polysorbate 80. In other embodiments, the ionizable lipid is 50 Mol %, the structural lipid is 10 Mol % DSPC, the sterol is from 37-40 Mol %, and the surfactant is about 0.5 Mol % to 2.5 Mol %. In embodiments of the invention, the surfactant comprises about 2.5 Mol % polyoxyethylene (10) stearyl ether. In embodiments of the invention, the surfactant comprises about 1.5 Mol % polysorbate 80. In embodiments of the invention, the surfactant comprises about 0.5 Mol % polyoxyethylene (40) stearate. In embodiments of the invention, the surfactant comprises about 0.5 Mol % D-α-Tocopherol polyethylene glycol 1000 succinate.

In embodiments of the invention, the lipid mix compositions of the invention cells are especially suited for T cell transfection.

In embodiments of the invention there is provided a method of treating T cells in vitro comprising isolating T cells from a bodily fluid, and contacting said cells with a nucleic acid therapeutic encapsulated in a lipid mix composition according to embodiments of the invention.

In embodiments of the method of the invention, the T cells are about to begin, or are in the log phase of growth, when contact is made. In embodiments, contact is made from day 3 to day 7 of cell culture. In preferred embodiments, contact is made on day 3 of cell culture. In another embodiment, the contact is made on day 7 of cell culture.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

DETAILED DESCRIPTION

Figure 1:
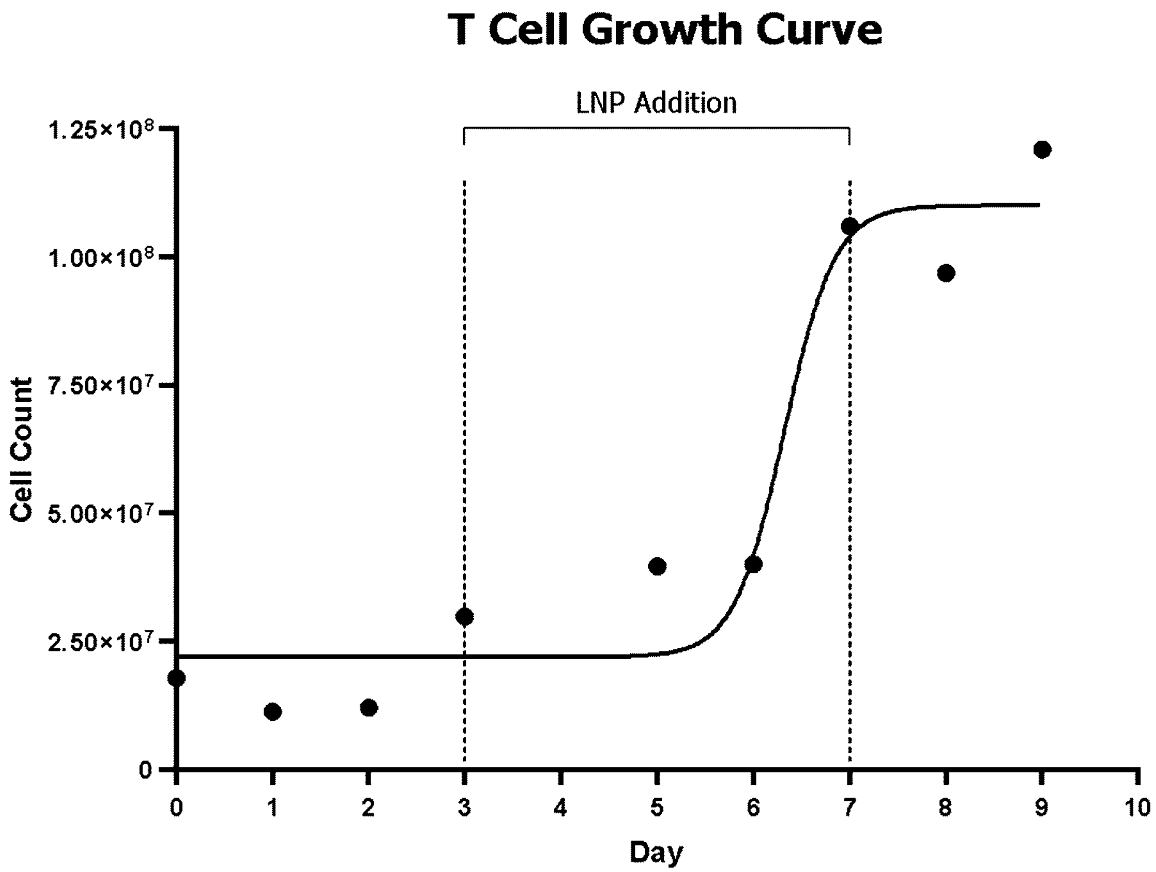
FIG. 1 is a linear plot of the growth (cell count) over time of isolated T cells following activation.

The present invention provides lipid mix compositions, their use in generating lipid mix compositions of nucleic acid therapeutics and other oligomers such as peptides, and methods for using these lipid mixes and resulting lipid mix compositions to overcome transfection-resistant cell types.

In another aspect, the lipid mix compositions of the invention are provided for mixing with nucleic acid therapeutics to create a lipid nucleic acid particle which enhances delivery of the nucleic acid into target cells or tissues, with less toxicity than more traditional lipid mix compositions or lipid nucleic acid particles such as those made from commercially available lipid mixes such as Lipofectamine™ or Transfectamine™ transfecting agents.

In another aspect, the invention provides lipid mix compositions including ionizable lipid, one or more structural lipid(s), cholesterol, and a particular surfactant.

In another aspect, the lipid mix compositions according the invention are provided for formulating nucleic acid and peptide therapeutics for the treatment of diseases of the central nervous system, or for cell reprogramming, or for ex vivo transformation of human T cells "Lipid" refers to structurally diverse group of organic compounds that are fatty acid derivatives or sterols or could be lipid like materials as in lipidoids (example C12-200) and are characterized by being insoluble in water but soluble in many organic solvents.

"Lipid Particles". The invention provides lipid particles manufactured from the lipid mix compositions described above. The lipid particle represents the physical organization of the lipid mix composition and a therapeutic agent. A lipid nanoparticle ("LNP") is a small, semi-to-fully organized lipid particle. Lipid nucleic acid particles or LNAP are generally spherical assemblies of lipids, nucleic acid, cholesterol and stabilizing agents. Positive and negative charges, ratios, as well as hydrophilicity and hydrophobicity of the elements dictate the physical structure of the lipid particles in terms of orientation of components and LNAP dimensions. The structural organization of lipid particles may lead to an aqueous interior with a minimum bilayer as in liposomes[6] or it may have a solid interior as in solid nucleic acid lipid nanoparticles.[7] There may be phospholipid monolayers or bilayers in single or multiple forms.[8] LNAP is a subgroup of Lipid Particles or LNP, because the inclusion of nucleic acid is specified.

As used herein, "N/P" is the ratio of moles of the amine groups of ionizable lipids to those of the phosphate groups of nucleic acid. In embodiments of the invention, N/P ratios are from 4 to 12, and most preferred ratios are from N/P 8-10. In one embodiment the N/P ratio is 10. In a preferred embodiment, the N/P ratio is 8.

"Lipid mix compositions" refers to the types of components, ratios of components, and the ratio of the total components to the nucleic acid payloads. For example, a lipid mix composition of 40 Mol % ionizable lipid, 20 Mol % structural lipid, 17 Mol % sterol, and 2.5 Mol % surfactant would be one lipid mix composition. The nucleic acid component is associated with this lipid mix composition to form a lipid nucleic acid particle, or LNP, in a premeditated ratio such as ionizable lipid amine (N) to nucleic acid phosphate ratio (P) of N/P 4, N/P 6, N/P 8, N/P 10, N/P 12 or another relevant particular N/P ratio.

"Viability" when referring to cells in vitro, means the ability to continue to grow, divide, and continue to grow and divide, as is normal for the cell type or tissue culture strain. Cell viability is affected by harsh conditions or treatments. Cell viability is critical in ex vivo therapy or parenteral administration.

"Ionizable lipid." The lipid particles include an ionizable lipid. As used herein, the term "ionizable lipid" refers to a lipid that is cationic or becomes ionizable (protonated) as the pH is lowered below the pKa of the ionizable group of the lipid, but is more neutral at higher pH values. At pH values below the pKa, the lipid is then able to associate with negatively charged nucleic acids (e.g., oligonucleotides). As used herein, the term "ionizable lipid" includes zwitterionic lipids that assume a positive charge on pH decrease, and any of a number of lipid species that carry a net positive charge at a selective pH, such as physiological pH. Such lipids include, but are not limited to, N,N-dioleyl-N,N-dimethyl-ammonium chloride (DODAC); 1,2-dioleoyl-3-dimethyaminopropane (DODAP), N-(2,3-dioleyloxy)propyl)-N,N,N-trimethylammonium chloride (DOTMA); N,N-distearyl-N,N-dimethylammonium bromide (DDAB); N-(2,3-dioleoyloxy)propyl)-N,N,N-trimethylammonium chloride (DOT AP); 3-(N—(N',N'-dimethylaminoethane)-carbamoyl) cholesterol (DC-Chol), and N-(1,2-dimyristyloxyprop-3-yl)-N,N-dimethyl-N-hydroxyethyl ammonium bromide (DMRIE).

In other preferred embodiments, the ionizable lipid is an amino lipid. In preferred embodiments of the invention, the ionizable lipid is 1,17-bis(2-octylcyclopropyl)heptadecan-9-yl 4-(dimethylamino) butanoate hydrochloride ("BOCHD-C3-DMA"). This compound is disclosed in United States Published Application No. 2013323269. In other preferred embodiments, the ionizable lipid is heptatriaconta-6,9,28,31-tetraen-19-yl 4-(dimethylamino)butanoate (Dlin-MC3-DMA or "MC3"). In other preferred embodiments, the ionizable lipid is 2,2-dilinoleyl-4-(2-dimethylaminoethyl)-[1,3]-dioxolane (Dlin-KC2-DMA or "KC2"). In other preferred embodiments, the ionizable lipid is (1,1'-((2-(4-(2-((2-(bis(2-hydroxydodecyl)amino)ethyl) (2-hydroxydodecyl) amino) ethyl) piperazin-1-yl) ethyl) azanediyl) bis(dodecan-2-ol)) or "C12-200".

In other embodiments, cationic lipids suitable for use in a lipid nanoparticle of the invention include, but are not limited to: DLenDMA; 98N12-5; reLNPs; KL 22 as described in United States Patent Publication 20120295832 A1, HGT5001, also called CCBene; HGT 4003, HGT 5000, HGT 5001, HGT5002 all as disclosed by Ball, R et al. in PCT publication nos. WO2020047061 A 1 and WO2013/14910, and by Derosa, Frank et al., in U.S. Ser. No. 10/507,183 BB; Lipidoids as mentioned in United States Patent Pub. No. 20180333366A 1, ATX-002 as described by Payne et al. in U.S. Ser. No. 10/399,937 BB; ATX-57, ATX-58, ATX-81, ATX-88 as described in U.S. Pat. No. 10,383,952 B2, 2-(1,2-di((9Z,12Z)-octadeca-9,12-dien-1-yl)hydrazinyl)-N,N-dimethylethan-1-amine), 4-(dimethylamino)-N',N'-di((9Z,12Z)-octadeca-9,12-dien-1-ylbutanehydrazide, 2-(di((9Z,12,Z)-octadeca-9,12-dien-1-yl)amino) ethyl 4-(dimethylamino)butanoate, 2-(di((9Z,12Z)-octadeca-9,12-dien-1-yl)amino)ethyl, and 4-(4-methylpiperazin-1-yl)butanoate as described in United States Patent Pub. No. 2019292130 A1.

Other suitable amino lipids useful in the invention also include those described in PCT patent publication no. WO 2009/096558. Representative amino lipids include 1,2-dilinoleyoxy-3-(dimethylamino)acetoxypropane (Dlin-DAC), 1,2-dilinoleyoxy-3-morpholinopropane (Olin-MA), 1,2-dilinoleoyl-3-dimethylaminopropane (DIinDAP), 1,2-dilinoleylthio-3-dimethylaminopropane (Dlin-S-DMA), 1-linoleoyl-2-linoleyloxy-3-dimethylaminopropane (Dlin-2-DMAP), 1,2-dilinoleyloxy-3-trimethylaminopropane chloride salt (Dlin-TMA-CI), 1,2-dilinoleoyl-3-trimethylaminopropane chloride salt (Dlin-TAP-CI), 1,2-dilinoleyloxy-3-(N-methylpiperazino)propane (Dlin-MPZ), 3-(N,N-dilinoleylamino)-1,2-propanediol (DIinAP), 3-(N,N-dioleylamino)-1,2-propanedio (DOAP), 1,2-dilinoleyloxo-3-(2-N, N-di methylamino)ethoxypropane (Dlin-EG-DMA), 2,2-dilinoleyl-4-dimethylaminomethyl-[I,3]-dioxolane (Dlin-K-DMA), 1,2-dilinoleyloxy-N,N-dimethyl-3-aminopropane (Dlin-DMA), and 1,2-dioleyloxy-3-dimethylaminopropane (DODMA).

In still other embodiments, ionizable lipids referred to in US20180000953 by Almarsson, Orn And Lawlor, Ciaran Patrick such as 3-(didodecylamino)-N1,N1,4-tridodecyl-1-piperazineethanamine (KL 10), 14,25-ditridecyl-15,18,21,24-tetraaza-octatriacontane (KL25), 2-(9oxy)-N,N-dimethyl-3-[(9Z,2Z)-octadeca-9,12-dien-1-yloxy]propan-1-amine (Octyl-Clin OMA), (2R)-2-(9oxy)-N,N-dimethyl-3-[(9Z-,12Z)-octadeca-9,12-dien-1-yl oxy]propan-1-amine (Octyl-ClinDMA (2R)), and (2S)-2-(9oxy)-N,N-dimethyl-3-[(9Z,1-2Z)-octadeca-9,12-dien-1-yl oxy]propan-1-amine (Octyl-ClinDMA (2S)) are employed.

The ionizable lipid is present in embodiments of the composition and lipid particle of the invention preferably comprise an amount from about 35 to about 55 Mol %, or more preferably 40 to about 50 Mol %.

Structural lipids are also known as "helper lipids" or "neutral lipids". The composition and lipid particles of the invention include one or more structural lipids at about 10 to 20 Mol % of the composition. Suitable structural lipids are believed to support the formation of particles. Structural lipids refer to any one of a number of lipid species that exist in either in an anionic, uncharged or neutral zwitterionic form at physiological pH. Representative structural lipids include diacylphosphatidylcholines, diacylphosphatidylethanolamines, diacylphosphatidylglycerols, ceramides, sphingomyelins, dihydrosphingomyelins, cephalins, and cerebrosides.

Exemplary structural lipids include zwitterionic lipids, for example, distearoylphosphatidylcholine (DSPC), dioleoylphosphatidylcholine (DOPC), dipalmitoylphosphatidylcholine (DPPC), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearoyl-2-oleoyl-phosphatidyethanol amine (SOPE), and 1,2-dielaidoyl-sn-glycero-3-phophoethanolamine (trans DOPE). In a preferred embodiment, the structural lipid is distearoylphosphatidylcholine (DSPC).

In another embodiment, the structural lipid is any lipid that is negatively charged at physiological pH. These lipids include phosphatidylglycerols such as dioleoylphosphatidylglycerol (DOPG), dipalmitoylphosphatidylglycerol (DPPG), palmitoyloleyolphosphatidylglycerol (POPG), cardiolipin, phosphatidylinositol, diacylphosphatidylserine, diacylphosphatidic acid, and other anionic modifying groups joined to neutral lipids. Other suitable structural lipids include glycolipids (e.g., monosialoganglioside GM1).

Stabilizing agents are included in lipid mix compositions and lipid nucleic acid embodiments to ensure integrity of the mixture among other actions not fully understood. Stabilizing agents are a class of molecules which disrupt or help form the hydrophobic-hydrophilic interactions among molecules. Examples of stabilizing agents include: Polysorbates (Tweens), and stabilizing lipid combinations including polysorbate and maltoside, Alkyl polyglycosides, Sorbitan esters (Spans), Polyoxyethylene alkyl esters, Polyoxyethylene alkyl ethers, Poloxamers, and PEG-conjugated lipids. Preferred stabilizing lipids according to embodiments of the invention include:

Brij™ S10, also known as Polyoxyethylene (10) stearyl ether, Brij™ S20, also known as Polyoxyethylene (20) stearyl ether, Brij™ L23, also known as Polyoxyethylene

(23) lauryl ether, Brij™ 35, linear Formula: (C2H4O) nC12H2GO, CAS Number: 9002-92-0; Brij™ L4, also known as Polyoxyethylene (4) lauryl ether polysorbate 80 or Tween® 80 also known as polysorbate 80, and Myrj52, also known as polyoxyethylene (40) stearate. Suitable stabilizing agents include polysorbate 80 (also known as Tween 80, IUPAC name 2-[2-[3,4-bis(2-hydroxyethoxy)oxolan-2-yl]-2-(2-hydroxyethoxy)ethoxy]ethyl octadec-9-enoate), Myrj52 (Polyoxyethylene (40) stearate, CAS Number: 9004-99-3), Brij™ S10 (Polyoxyethylene (10) stearyl ether, CAS Number: 9005-00-9), Brij™ S20, (Polyoxyethylene (20) stearyl ether, CAS Number: 9005-00-9), Brij™35 (Polyoxyethylene monolauryl ether, CAS [9002-92-0]), Brij™ L4 (Polyethylene glycol dodecyl ether, Polyoxyethylene (4) lauryl ether, CAS Number 9002-92-0), and TPGS-1000 (D-α-Tocopherol polyethylene glycol 1000 succinate, CAS Number: 9002-96-4). The stabilizing agents may be used in mixtures and in combination.

In some embodiments, the surfactant comprises about 0.1 to 5 Mol % of the overall lipid mixture. In some embodiments, the surfactant comprises about 0.1 to 3 Mol % of the overall lipid mixture. In some embodiments, the surfactant comprises about 0.5 to 2.5 Mol % of the overall lipid mixture. In some embodiments, the surfactant is about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, and so forth.

Sterols are included in the preferred lipid mix compositions, and lipid particles made therefrom include sterols, such as cholesterol and phytosterol. In the lipid mixes of the invention, cholesterol is present at about 30 to 50 Mol % of the final lipid mix in some embodiments. Preferably, cholesterol is present at about 35 to 41 Mol % of the final lipid mix. Cholesterol is present as about 29.5, 39.5, 38.5, and 37.5 Mol % in various preferred embodiments. Sterols include molecules structurally related to cholesterol family, analogues, natural or synthetic in origin. Modified and naturally occurring plant sterols could be efficiently used instead of cholesterol. Patel Sidharth et. al. describes some naturally occurring sterols enhancing the mRNA delivery in cell line using a LNP. [6]

Peptides. The lipid mix compositions and lipid particles of the present invention are useful for the systemic or local delivery of peptides. As used herein, the term "therapeutic peptide" is meant to include any amino acid chain whose delivery into a cell causes a desirable effect. A peptide is a short chain of amino acids, two to 50 amino acids in length, as opposed to a protein which has a longer chain (50 amino acids or more), often with tertiary and/or quaternary structure. The amino acids in a peptide are connected to one another in a sequence by bonds called peptide bonds. In some embodiments, the peptide or peptides are encapsulated with nucleic acid(s).

Nucleic Acids. The lipid mix compositions and lipid particles of the present invention are useful for the systemic or local delivery of nucleic acids. As used herein, the term "nucleic acid therapeutic" (NAT) is meant to include any oligonucleotide or polynucleotide whose delivery into a cell causes a desirable effect. Fragments containing up to 50 nucleotides are generally termed oligonucleotides, and longer fragments are called polynucleotides. In particular embodiments, oligonucleotides of the present invention are 8-50 nucleotides in length. In embodiments of the invention, oligonucleotides are 996 to 4500 nucleotides in length, as in the case of messenger RNA. In other embodiments of the invention, the messenger RNA is self-amplifying mRNA. Currently, NATs are being actively pursued in an increasing number of pre-clinical and clinical studies. These NATs include deoxyribonucleic acid, complementary deoxyribonucleic acid, complete genes, ribonucleic acid, oligonucleotides and ribozymes for gene therapies targeting a variety of diseases, such as cancer, infectious diseases, genetic disorders and neurodegenerative diseases. NAT have shown clinical utility in Onpattro™ patisirin. Self-amplifying mRNa and other mRNAs (WT and base modified) are being evaluated as vaccines for infectious diseases (mRNA-1273 for COVID-19, mRNA 1944 for chikungunya), rare diseases (mRNA-3704 for methylmalonic acidemia).

As described herein, the nucleic acid therapeutic (NAT) is incorporated into the lipid particle during its formation. More than one nucleic acid therapeutic may be incorporated in this way. "LNAP" refers to the NAT in a lipid nanoparticle.

The nucleic acid that is present in a lipid particle according to this invention includes any form of nucleic acid that is known. The nucleic acids used herein can be single-stranded DNA or RNA, or double-stranded DNA or RNA, or DNA-RNA hybrids. Examples of double-stranded DNA include structural genes, genes including control and termination regions, and self-replicating systems such as viral or plasmid DNA. Examples of double-stranded RNA include siRNA and other RNA interference reagents. Single-stranded nucleic acids include antisense oligonucleotides, guide RNA, including CRISPR-Cas9 gRNA, ribozymes, microRNA, mRNA, and triplex-forming oligonucleotides. More than one nucleic acid may be incorporated into the lipid particle, for example mRNA and guide RNA together, or different types of each.

Plasmid DNA is a preferred nucleic acid formulated in embodiments of the invention. A plasmid is a DNA molecule that is separate from chromosomal DNA in a cell, and can replicate independently. Plasmids range from less than 1000 nucleotides to tens of thousands of nucleotides in size. The most common form is small circular, double-stranded DNA. Plasmids can be synthesized and delivered to mammalian cells for therapeutic purposes. Synthetic plasmids are used as vectors in molecular cloning, serving to drive the replication of recombinant DNA sequences within host organisms. Plasmids may be introduced into cells via transformation using physical methods such as electroporation, or chemical means as in the present invention, via lipid particle-enhanced transfection. These lipid mix compositions of the invention have several advantages over physical techniques, including i) high biocompatibility and low toxicity in cell and tissue systems ii) relative ease of manufacture iii) lipophilic matrices are less susceptible to the erosion phenomena observed in polymeric systems iv) an increased circulatory half-life in vivo due to their invisibility from the immune system.

Thus, in one embodiment, the nucleic acid therapeutic (NAT) is a plasmid or circular nucleic acid construct or a linearized DNA. In one embodiment, the NAT is an mRNA or self-amplifying mRNA.

In some cases, a nucleic acid encodes a genetically engineered receptor that specifically binds to a ligand, such as a recombinant receptor, and a molecule involved in a metabolic pathway, or functional portion thereof. Alternately, the molecule involved in a metabolic pathway is a recombinant molecule, including an exogenous entity. A genetically engineered receptor and the molecule involved in a metabolic pathway may be encoded by one nucleic acid or two or more different nucleic acids. In some examples, a first nucleic acid might encode a genetically engineered receptor that specifically binds to a ligand and a second nucleic acid might encode the molecule involved in a metabolic pathway.

The nucleic acid may be structured to co-express multiple, separate peptide chains from the same promoter. The transcript may have the potential to code for more than one final product, such as two final products. At least one of the nucleic acids may have an internal ribosome binding site (IRES) separating the encoded molecules such that the genetically engineered receptor and the molecule involved in a metabolic pathway are expressed under the control of the same promoter. An "internal ribosome entry site" (IRES) is a nucleotide sequence that allows for translation initiation in the middle of a messenger RNA (mRNA) sequence as part of protein synthesis. In some embodiments, the nucleic acid includes one or more ribosomal skip sequences, such as picornavirus 2A ribosomal skip peptide, so that the two or more peptide chains or other products may be expressed in operable linkage with the same promoter, but produced as separate chains.

In some situations, a single promoter may direct expression of an RNA that contains, in a single open reading frame (ORF), two or three genes separated from one another by sequences encoding a self-cleavage peptide (e.g., 2A sequences) or a protease recognition site (e.g., furin).

In some embodiments, expression or activity of the genetically engineered or recombinant receptor and/or of the recombinant or engineered molecule involved in a metabolic pathway is constitutive; in some embodiments, one or more of such expression or activity is engineered to be conditional, for example, induced or repressed by one or more natural or non-natural events or molecules.

In some embodiments, expression of the receptor and/or the molecule is under the control of a constitutive promoter, enhancer, or transactivator. In some embodiments, the expression is under the control of a conditional promoter, enhancer or transactivator.

In some examples, the expression of the molecule or receptor, generally the molecule, is conditional upon (e.g., is induced or repressed by, such as via an inducible promoter or other element) by one or more specific conditions, events, or molecules found or found at relatively higher levels in particular, regions of the body, disease, activation state, or tissues. For example, in some examples the promoter can be inducible or suppressible by hypoxia, glucose-poor or other nutrient-poor conditions. See, e.g. Cao, et al. (2001) Gene Ther., 8: 1357-1362 and Dachs, et al. (2000) Eur. J. Cancer, 36:1649-1660, and Greco et al., (2002) Gene Ther., 9:1403-1411. In other expression control types, expression is regulated by activation or proliferative events. Exemplary inducible systems are those activatable by NFkappaB, NFAT or Nur77.

In some embodiments, expression of any of the peptides or nucleic acids described herein may be controlled by treating the cell with a modulating factor, such as doxycycline, tetracycline or analogues thereof.

Specific examples of transcription modulator domains that induce or reduce expression in the presence of modulating factor include, but are not limited to, the transcription modulator domains found in the following transcription modulators: the Tet-On™ transcription modulator; the Tet-Off™ transcription modulator, and the Tet-On™ Advanced transcription modulator and the Tet-On™ 3G transcription modulator; all of which are available from Clontech Laboratories, Mountain View, Calif.

In some embodiments, suitable promoters include, for example, CMV, RNA polymerase (pol) III promoters including, but not limited to, the (human and murine) U6 promoters, the (human and murine) H1 promoters, and the (human and murine) 7SK promoters, including conditional variants thereof. In some embodiments, a hybrid promoter also can be prepared that contains elements derived from, for example, distinct types of RNA polymerase (pol) III promoters. In some embodiments, the promoter sequence can be one that does not occur in nature, so long as it functions in a eukaryotic cell, such as, for example, a mammalian cell.

The term "nucleic acids" also refers to ribonucleotides, deoxynucleotides, modified ribonucleotides, modified deoxyribonucleotides, modified phosphate-sugar-backbone oligonucleotides, other nucleotides, nucleotide analogs, and combinations thereof, and can be single stranded, double stranded, or contain portions of both double stranded and single stranded sequence, as appropriate. Messenger RNA can be modified or unmodified, base modified, and may include different type of capping structures, such as Cap1.

As used herein, the terms "polynucleotide" and "oligonucleotide" are used interchangeably and mean single-stranded and double-stranded polymers of nucleotide monomers, including 2'-deoxyribonucleotides (DNA) and ribonucleotides (RNA) linked by internucleotide phosphodiester bond linkages, e.g., 3'-5' and 2'-5', inverted linkages, e.g., 3'-3' and 5'-5', branched structures, or internucleotide analogs. Polynucleotides have associated counter ions, such as H+, NH4+, trialkylammonium, Mg2+, Na+, and the like. A polynucleotide may be composed entirely of deoxyribonucleotides, entirely of ribonucleotides, or chimeric mixtures thereof. Polynucleotides may be made up of internucleotide, nucleobase and/or sugar analogs.

As used herein, "nucleic acid" is a nucleobase sequence-containing polymer, or polymer segment, having a backbone formed from nucleotides, or analogs thereof.

The lipid particles according to some embodiments of the invention can be characterized by electron microscopy. The particles of the invention having a substantially solid core have an electron dense core as seen by electron microscopy. One such structure is disclosed in U.S. Pat. No. 9,758,795 by Cullis et al. Electron dense is defined such that area-averaged electron density of the interior 50% of the projected area of a solid core particle (as seen in a 2-D cryo EM image) is not less than x % (x=20%, 40%, 60%) of the maximum electron density at the periphery of the particle. Electron density is calculated as the absolute value of the difference in image intensity of the region of interest from the background intensity in a region containing no nanoparticle.

The lipid particles of the invention can be assessed for size using devices that size particles in solution, such as the Malvern™ Zetasizer™. The particles have a mean particle diameter from about 15 to about 300 nm. In some embodiments, the mean particle diameter is greater than 300 nm. In some embodiments, the lipid particle has a diameter of about 300 nm or less, 250 nm or less, 200 nm or less, 150 nm or less, 100 nm or less, or 50 nm or less. In one embodiment, the lipid particle has a diameter of from about 50 to about 150 nm. Smaller particles generally exhibit increased circulatory lifetime in vivo compared to larger particles. In one embodiment, the lipid particle has a diameter from about 15 to about 50 nm. Ex vivo applications do not require as small a particle as does in vivo applications.

Mixing. The lipid particles according to embodiments of the invention can be prepared by standard T-tube mixing techniques, turbulent mixing, trituration mixing, agitation promoting orders self-assembly, or passive mixing of all the elements with self-assembly of elements into nanoparticles.

A variety of methods have been developed to formulate lipid nanoparticles (LNP) containing genetic drugs (LNAP). Suitable methods are disclosed in U.S. Pat. No. 5,753,613 by Ansell, Mui and Hope and U.S. Pat. No. 6,734,171 by Saravolac et al., by way of example. These methods include mixing preformed lipid particles with nucleic acid therapeutic (NAT) in the presence of ethanol or mixing lipid dissolved in ethanol with an aqueous media containing NAT.

Microfluidic two-phase droplet techniques have been applied to produce monodisperse polymeric microparticles for drug delivery or to produce large vesicles for the encapsulation of cells, proteins, or other biomolecules. The use of hydrodynamic flow focusing, a common microfluidic technique to provide rapid mixing of reagents, to create monodisperse liposomes of controlled size has been demonstrated.

In general, parameters such as the relative lipid and NAT concentrations at the time of mixing, as well as the mixing rates are difficult to control using current formulation procedures, resulting in variability in the characteristics of NAT produced, both within and between preparations. Automatic micro-mixing instruments such as the NanoAssembr™ instruments (Precision NanoSystems Inc, Vancouver, Canada) enable the rapid and controlled manufacture of nanomedicines (liposomes, lipid nanoparticles, and polymeric nanoparticles). NanoAssembr™ instruments accomplish controlled molecular self-assembly of nanoparticles via microfluidic mixing cartridges that allow millisecond mixing of nanoparticle components at the nanoliter, microlitre, or larger scale with customization or parallelization. Rapid mixing on a small scale allows reproducible control over particle synthesis and quality that is not possible in larger instruments.

Preferred methods incorporate instruments such as the microfluidic mixing devices like the NanoAssembr™ Spark™, Ingnite™ or its predeccesor, the Benchtop™, and Blaze™, in order to achieve nearly 100% of the nucleic acid used in the formation process is encapsulated in the particles in one step. In one embodiment, the lipid particles are prepared by a process by which from about 90 to about 100% of the nucleic acid used in the formation process is encapsulated in the particles.

U.S. Pat. Nos. 9,758,795 and 9,943,846, by Cullis et al. describe methods of using small volume mixing technology and novel formulations derived thereby. U.S. Pat. No. 10,342,760 by Ramsay et al. describes more advanced methods of using small volume mixing technology and products to formulate different materials. U.S. Pat. No. 10,159,652 by Walsh, et al. discloses microfluidic mixers with different paths and wells to elements to be mixed. United States Patent Pub. No. 20180111830 AA by Wild, Leaver and Taylor discloses microfluidic mixers with disposable sterile paths. U.S. Pat. No. 10,076,730 by Wild, Leaver and Taylor discloses bifurcating toroidal microfluidic mixing geometries and their application to micromixing. United States Patent Pub. No. 2020023358 AA by Chang, Klaassen, Leaver et al. discloses a programmable automated micromixer and mixing chips therefor. United States Design Nos. D771834, D771833, D772427, and D80341 6, by Wild and Weaver, and D800335, D800336 and D812242 by Chang et al. disclose mixing cartridges having microchannels and mixing geometries for mixer instruments sold by Precision NanoSystems Inc.

In embodiments of the invention, devices for biological microfluidic mixing are used to prepare the lipid particles and therapeutic lipid mix compositions of the invention. The devices include a first and second stream of reagents, which feed into the microfluidic mixer, and lipid particles are collected from the outlet, or in other embodiments, emerge into a sterile environment.

The first stream includes a therapeutic agent in a first solvent. Suitable first solvents include solvents in which the therapeutic agents are soluble and that are miscible with the second solvent. Suitable first solvents include aqueous buffers. Representative first solvents include citrate and acetate buffers.

The second stream includes lipid mix materials in a second solvent. Suitable second solvents include solvents in which the ionizable lipids are soluble and that are miscible with the first solvent. Suitable second solvents include 1,4-dioxane, tetrahydrofuran, acetone, acetonitrile, dimethyl sulfoxide, dimethylformamide, acids, and alcohols. Representative second solvents include aqueous ethanol 90%, or anhydrous ethanol.

In one embodiment of the invention, a suitable device includes one or more microchannels (i.e., a channel having its greatest dimension less than 1 millimeter). In one example, the microchannel has a diameter from about 20 to about 300 μm. In examples, at least one region of the microchannel has a principal flow direction and one or more surfaces having at least one groove or protrusion defined therein, the groove or protrusion having an orientation that forms an angle with the principal direction (e.g., a staggered herringbone mixer), as described in United States Patent Pub. No. 20040262223 AA, or a bifurcating toroidal flow as described in United States Patent Pub. No. 2018093232 AA. To achieve maximal mixing rates, it is advantageous to avoid undue fluidic resistance prior to the mixing region. Thus, one example of a device has non-microfluidic channels having dimensions greater than 1000 microns, to deliver the fluids to a single mixing channel.

Less automated microfluidic mixing methods and instruments such as those disclosed in Zhang, S., et al.[8] and Stroock A., et al.[9] are also useful in creating lipid mix compositions of the invention. More primitive systems involving T-tube mixing are disclosed in Jeffs, L B et al. [0].

The lipid particles of the present invention may be used to deliver a therapeutic agent to a cell, in vitro or in vivo. In particular embodiments, the therapeutic agent is a nucleic acid, which is delivered to a cell using nucleic acid-lipid particles of the present invention. The nucleic acid can be an siRNA, miRNA, an LNA, a plasmid or replicon, an mRNA, or a single gene. In other embodiments, the therapeutic agent is a peptide, which is delivered to a cell using peptide-lipid particles of the present invention. The methods and lipid mix compositions may be readily adapted for the delivery of any suitable therapeutic agent for the treatment of any disease or disorder that would benefit from such treatment.

In certain embodiments, the present invention provides methods for introducing a nucleic acid into a cell (i.e.transfection). Transfection is a technique commonly used in molecular biology for the introduction of nucleic acid therapeutics (or NATs) from the extracellular to the intracellular space for the purpose of transcription, translation and expression of the delivered gene(s). Transfection efficiency is commonly defined as either the i) percentage of cells in the total treated population showing positive expression of the delivered gene, as measured by protein quantification methods such as live cell imaging (for detection of fluorescent protein), flow cytometry or ELISA, or ii) the intensity or amount of protein expressed by treated cell(s). These methods may be carried out by contacting the particles or lipid mix compositions of the present invention with the cells for a period of time sufficient for intracellular delivery to occur.

Typical applications include using well known procedures to provide intracellular delivery of siRNA to knock down or silence specific cellular targets. Alternatively, applications include delivery of DNA or mRNA sequences that code for therapeutically useful polypeptides. In this manner, therapy is provided for genetic diseases by supplying deficient or absent gene products. Methods of the present invention may be practiced in vitro, ex vivo, or in vivo. For example, the lipid mix compositions of the present invention can also be used for delivery of nucleic acids to cells in vivo, using methods which are known to those of skill in the art. In another example, the lipid mix compositions of the invention can be used for delivery of nucleic acids to a sample of patient cells that are ex vivo, then are returned to the patient.

The delivery of nucleic acid therapeutics by lipid compositions of the invention is described below.

For in vivo administration, the pharmaceutical compositions are preferably administered parenterally (e.g., intraarticularly, intravenously, intraperitoneally, subcutaneously, intrathecally, intradermally, intratracheally, intraosseous or intramuscularly). In particular embodiments, the pharmaceutical compositions are administered intravenously, intrathecally, or intraperitoneally by a bolus injection. Other routes of administration include topical (skin, eyes, mucus membranes), oral, pulmonary, intranasal, sublingual, rectal, and vaginal.

For ex vivo applications, the pharmaceutical compositions are preferably administered to biological samples that have been removed from the organism, then the cells are washed and restored to the organism. The organism may be a mammal, and in particular may be human. This process is used for cell reprogramming, genetic restoration, immunotherapy, for example. The drug product is the modified cell. Examples of current cell products available commercially for immuno-oncology applications are Kymriah™ for B cell precursor acute lymphoblastic leukemia and Yescarta™ for use in B cell lymphoma. This ex vivo therapy is also called as CAR-T therapy wherein modified T cells with CD19-targeted chimeric antigen receptor attacks the CD19 presenting cancer cells of the patient. Leukemia is the leading cause of mortality in pediatric patients. Use of CAR-T therapy was transformative to the patient's cancer free recovery.

In one embodiment, the present invention provides a method of modifying human T cells with chimeric antigen receptor (CAR) encoded mRNA to produce CAR-T cell product to be infused back into the patient, without any viral means of delivery of nucleic acid. Non-viral delivery can be a safer technology for modulating the T cell than a virus for programming the cells.

In related embodiments, the present invention provides a method of modulating the T cell receptors to recognize and destroy neoantigens present on the surface of the tumor cells of the patient.

In one embodiment, the present invention provides a method of modulating the expression of a target polynucleotide or polypeptide. These methods generally comprise contacting a cell with a lipid particle of the present invention that is associated with a nucleic acid capable of modulating the expression of a target polynucleotide or polypeptide. As used herein, the term "modulating" refers to altering the expression of a target polynucleotide or polypeptide. Modulating can mean increasing or enhancing, or it can mean decreasing or reducing.

In related embodiments, the present invention provides a method of treating a disease or disorder characterized by overexpression of a polypeptide in a subject, comprising providing to the subject a pharmaceutical composition of the present invention, wherein the therapeutic agent is selected from an siRNA, a microRNA, an antisense oligonucleotide, and a plasmid capable of expressing an siRNA, a microRNA, or an antisense oligonucleotide, and wherein the siRNA, microRNA, or antisense RNA comprises a polynucleotide that specifically binds to a polynucleotide that encodes the polypeptide, or a complement thereof.

In related embodiments, the present invention provides a method of treating a disease or disorder characterized by under-expression of a polypeptide in a subject, comprising providing to the subject a pharmaceutical composition of the present invention, wherein the therapeutic agent is selected from an mRNA, a self-amplifying RNA (SAM), a self-replicating DNA, or a plasmid, comprises a nucleic acid therapeutic that specifically encodes or expresses the under-expressed polypeptide, or a complement thereof.

In embodiments, lipid mix compositions of the pharmaceutical compositions described herein may be prepared by any method known or hereafter developed according to the pharmacology principles. In general, such preparatory methods include the step of associating the active ingredient with an excipient and/or one or more other accessory ingredients.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient may generally be equal to the dosage of the active ingredient which would be administered to a subject and/or a convenient fraction of such a dosage including, but not limited to, one-half or one-third of such a dosage.

In another embodiment, the composition is used to produce an Advanced Therapy Medicinal Product (ATMP) or cell and gene therapy products. The compositions described herein can be considered as ancillary materials.

Relative amounts of the active ingredient, the pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may comprise between 0.1 percent and 99 percent (w/w) of the active ingredient.

Pharmaceutical formulations may additionally comprise a pharmaceutically acceptable excipient, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21st Edition, A. R. Gennaro, Lippincott, Williams and Wilkins, Baltimore, MD, 2006).

In some embodiments, the particle size of the lipid particles may be increased and/or decreased. The change in particle size may be able to help counter biological reactions such as, but not limited to, inflammation or may increase the biological effect of the NAT delivered to mammals by changing biodistribution. Size may also be used to determine target tissue, with larger particles being cleared quickly and smaller one reaching different organ systems.

Pharmaceutically acceptable excipients used in the manufacture of pharmaceutical compositions include, but are not limited to, inert diluents, surface active agents and/or emulsifiers, preservatives, buffering agents, lubricating agents, and/or oils. Such excipients may optionally be included in the pharmaceutical formulations of the invention.

In some embodiments, exemplary plasmid or other NAT encodes the protein or enzyme selected from human growth hormone, erythropoietin, a 1-antitrypsin, acid alpha glucosidase, arylsulfatase A, carboxypeptidase N, a-galactosidase A, alpha-L-iduronidase, iduronate-2-sulfatase, iduronate sulfatase, N-acetylglucosamine-1-phosphate transferase, N-acetylglucosaminidase, alpha-glucosaminide acetyltransferase, N-acetylglucosamine 6-sulfatase, N-acetylgalactosamine-4-sulfatase, beta-glucosidase, galactose-6-sulfate sulfatase, beta-galactosidase, beta-glucuronidase, glucocerebrosidase, heparan sulfamidase, heparin-N-sulfatase, lysosomal acid lipase, hyaluronidase, galactocerebrosidase, ornithine transcarbamylase (OTC), carbamoyl-phosphate synthetase 1 (CPS 1), argininosuccinate synthetase (ASS 1), argininosuccinate lyase (ASL), arginase 1 (ARGI), cystic fibrosis transmembrane conductance regulator (CFTR), survival motor neuron (SMN), Factor VIII, Factor IX, meganucleases like TALENS, Cas9 and self-replicating RNA's, and low density lipoprotein receptors (LDLR).

Other plasmid or nucleic acids can be applied to cell-based system using this invention in the context of a research or screening platform. These include the introduction of genetic material for the purpose of inducing specific physiological or functional changes in cells, such as in the process of reprogramming for the generation of induced pluripotent stem cells. In this case, specific genes (known as Yamanaka factors) are introduced to patient-derived somatic cells, which trigger a reversal of the cell to a stem cell-like state. These enable the cells to divide indefinitely and become pluripotent (able to differentiate to many other downstream cell types) which can be used for both research and clinical applications. These and similar genetic manipulation steps can be enhanced by the lipid particles of the invention to improve the efficiency of processes commonly used when working with induced stem cells.

In preferred embodiments, the nucleic acid is a plasmid composed of double stranded deoxyribonucleic acid. A plasmid is a genetic structure that resides in a cell's cytoplasm (as opposed to the nucleic where the traditional cellular genetics reside) cell that can replicate independently of the chromosomes, typically a small circular DNA strand. This a synthetic mammalian genetic construct used as a therapeutic option for manipulating the genetic function in a cell. Plasmids can also be used to create novel cellular or animal models for medical research. Plasmids are an important tool in molecular biology and as an emerging therapeutic due to their i) ease of manipulation and isolation ii) ability to self-replicate for scaled-up manufacturing iii) long term stability iv) functionality in a range of organisms and applications. An engineered plasmid will have, in addition to a replication origin (or not, depending on the intended use), restriction enzyme recognition sites to allow breaking the circle to introduce new genetic material, and a selective marker such as an antibiotic resistance gene. A plasmid may be from about 1000 base pairs (bp) to about 20 kilobase pairs (kbp).

As used herein, the term "about" is defined as meaning 10% plus or minus the recited number. It is used to signify that the desired target concentration might be, for example, 40 Mol %, but that through mixing inconsistencies, the actual percentage might differ by +/−5 Mol %.

As used herein, the term "substantially" is defined as being 5% plus or minus the recited number. It is used to signify that the desired target concentration might be, for example, 40 Mol %, but that through measuring or mixing inconsistencies, the actual percentage might differ by +/−5 Mol %.

As used herein, the term "nucleic acid" is defined as a substance intended to have a direct effect in the diagnosis, cure, mitigation, treatment or prevention of disease, or to have direct effect in restoring, correcting or modifying physiological functions, or to act as a research reagent. In preferred embodiments, the nucleic acid is an oligonucleotide. In preferred embodiments, the therapeutic agent is a nucleic acid therapeutic, such as an RNA polynucleotide. In preferred embodiments, the therapeutic agent is double stranded circular DNA (plasmid).

As used herein, the term "reagent" is defined by the fact that it has a direct influence on the biological effect of cells, tissues or organs. Reagents include but are not limited to polynucleotides, proteins, peptides, polysaccharides, inorganic ions and radionuclides. Examples of nucleic acid reagents include but are not limited to antisense oligonucleotides, ribozymes, microRNA, mRNA, ribozyme, tRNA, tracrRNA, sgRNA, snRNA, siRNA, shRNA, ncRNA, miRNA, mRNA, pre-condensed DNA, pDNA or an aptamer. Nucleic acid reagents are used to silence genes (with for example siRNA), express genes (with for example mRNA), edit genomes (with for example CRISPR/Cas9), and reprogram cells for return to the originating organism (for example ex vivo cell therapy to reprogram immune cells for cancer therapy). Ancillary material for ATMP (Advanced Therapy Medicinal Products) can be considered a reagent.

In this disclosure, the word "comprising" is used in a non-limiting sense to mean that items following the word are included, but items not specifically mentioned are not excluded. It will be understood that in embodiments which comprise or may comprise a specified feature or variable or parameter, alternative embodiments may consist, or consist essentially of such features, or variables or parameters. A reference to an element by the indefinite article "a" does not exclude the possibility that more than one of the elements is present, unless the context clearly requires that there be one and only one of the elements.

In this disclosure the recitation of numerical ranges by endpoints includes all numbers subsumed within that range including all whole numbers, all integers and all fractional intermediates (e.g., 1 to 5 includes 1, 1.5, 2, 2.75, 3, 3.80, 4, and 5 etc.). In this disclosure the singular forms an "an", and "the" include plural referents unless the content clearly dictates otherwise. Thus, for example, reference to a composition containing "a compound" includes a mixture of two or more compounds. In this disclosure term "or" is generally employed in its sense including "and/or" unless the content clearly dictates otherwise.

A T cell, or T lymphocyte, is a lymphocyte subtype that has the lead role in cell-mediated immunity. T cells can be distinguished from other white blood cells, (for example, B cells or natural killer cells), by the existence of a T cell receptor on the cell surface. The main categories of T cells include Helper (CD4+), Cytotoxic (CD8+), Memory and Regulatory T cells.

The log phase of growth with reference to T cell cultures means, for example, the time that the cells undergo a rapid expansion, around day 5 or day 6 post activation. Log phase can be observed through a sudden increase in cell count, this rapid expansion can be used as a time point to begin preparing LNPs for T cell treatment. In embodiments of the invention, T cells may be activated in different ways. The triple activation method using anti-CD3/CD28/CD2 antibodies is exemplified below, but dual activation was also effective in our studies. Dual activation is performed using anti CD3/CD28 antibodies. Current clinically used protocols employ the dual activation protocol.

T cells may in some cases be derived from differentiated from induced pluripotent stem cells (IPSC)" or Embryonic Stem Cells (ESC).[12]

Preparation of T cells for transformation by methods of the invention includes one or more culture and/or preparation steps. The T cells are usually isolated from biological tissue (such as peripheral blood or arterial blood) derived from a mammalian subject. In some embodiments, the subject from which the cell is isolated has a disease or condition or in need of a cell therapy or to which cell therapy will be administered.

The cells in some embodiments are primary cells, such as primary human cells. The tissue sources include blood, tissue, lymph, and other tissue sources taken directly from the subject, and samples resulting from one or more processing steps, such as separation, centrifugation, washing, and/or incubation.

The tissue source from which the T cells are derived may be a blood or a blood-derived tissue source, or an apheresis or leukapheresis product. Exemplary tissue sources include whole blood, peripheral blood mononuclear cells (PBMCs), leukocytes, bone marrow, thymus, tissue biopsy, tumor, lymph node, spleen, or other lymphoid tissues. The cells in some embodiments are obtained from a different species than the eventual subject needing therapy.

Isolation of the cells may include more preparation or non-affinity based cell separation. In some cases, cells are washed, centrifuged, and/or incubated in the presence of one or more reagents, for example, to remove or enrich for certain components.

In some cases, cells from the circulating blood of a subject are obtained by apheresis or leukapheresis. The blood cells may be washed to remove the plasma fraction, and an appropriate buffer or media is used for subsequent processing steps. In some embodiments, the cells are washed with phosphate buffered saline (PBS). In some aspects, a washing step is performed by tangential flow filtration (TFF) according to the manufacturer's instructions (Spectrum Krosflo, GE Akta Flux, for example). In some embodiments, the cells are resuspended in a variety of biocompatible buffers after washing, such as, for example, Ca++/Mg++ free PBS.

Separating the T cells from tissue sources may involve density-based cell separation methods, including the preparation of white blood cells from peripheral blood by lysing the red blood cells and centrifugation through a Percoll™ or Ficoll™ gradient. Other methods include the separation of different cell types based on the expression or presence in the cell of one or more specific surface markers.

Specific subpopulations of T cells, such as cells positive or expressing high levels of one or more surface markers, e.g., $CD28^+$, $CD62L^+$, $CCR7^+$, $CD27^+$, $CD127^+$, $CD4^+$, $CD8^+$, CD45RA+, and/or CD45RO+ T cells, can be isolated by positive or negative selection techniques. As one example, $CD3^+$, $CD28^+$ T cells can be positively selected using CD3/CD28 conjugated magnetic beads (e.g., OYNABEAOS® M-450 CD3/CD28 T Cell Expander). A $CD4^+$ or $CD8^+$ selection step can be used to separate CD4+ helper and CD8+ cytotoxic T cells. Memory T cells are present in both CD62L+ and CD62L-subsets of CD8+ peripheral blood lymphocytes. Alternatively, a selection for $CD4^+$ helper cells may be undertaken. In some cases, naive $CD4^+$ T lymphocytes are $CD45RO^-$, $CD45RA^+$, $CD62L^+$, CD4+ T cells. In others, central memory $CD4^+$ cells are $CD62L^+$ and $CD45RO^+$. In still other cases, effector CD4+ cells are $CD62L^-$ and CD45RO.

Cell populations can also be isolated using affinity magnetic separation techniques. The cells to be separated are incubated with magnetically responsive particles or microparticles, such as paramagnetic beads (e.g., Oynabeads™ (Clontech) or MACS™ (Miltenyi) beads). The magnetically responsive material is attached to a binding partner that specifically binds to a surface marker, present on the cell, cells, or population of cells that it is desired to separate.

T cells may be isolated by positive or negative selection processes from tissue sources depending on preference. Kits for both are available, for example, from StemCell Technologies in Vancouver, Canada.

For therapeutic purposes, isolation or separation is carried out using an apparatus that carries out one or more of the isolation, cell preparation, separation, processing, an incubation, required to transform the T cells. In some aspects, the system is used to carry out each of these steps in a closed or sterile environment. In one example, the system is a system as described in United States Patent Pub. No. 20110003380 A 1. Separation and/or other steps may be accomplished using the CliniMACS system (Miltenyi Biotec). See, e.g., Klebanoff et al. (2012) J Immunother. 35(9): 651-660, Terakura et al. (2012) Blood. 1:72-82, and Wang et al. (2012) J Immunother. 35(9):689-701. A desired cell population can be collected and enriched via flow cytometry, in which cells stained for multiple cell surface markers are carried in a fluid stream. Other methods include FACS or microelectromechanical systems (MEMS) chips in combination with a FAGS-based detection system (see, e.g., WO 2010/033140).

T cell incubation and treatment may be carried out in a culture vessel, such as a chamber, well, column, tube, tubing set, valve, vial, culture dish, bag, tank or other container for culture or cultivating cells. Stimulating conditions or agents include one or more agent, such as a ligand, capable of activating an intracellular signaling domain of a TCR complex. Incubation may be carried out as described in U.S. Pat. No. 6,040,177 to Riddell et al. T cell cultures can be expanded by adding non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture.

T cell stimulating conditions include temperatures suitable for the growth of human T lymphocytes, for example, from 25 to 37 degrees Celsius. Optionally, the incubation may further include a supportive population of non-dividing EBV-transformed lymphoblastoid cells (LCL) as feeder cells, at a ratio to initial T cells of 10 to 1.

The present invention will be more readily understood by referring to the following examples which are given to illustrate the invention rather than to limit its scope.

Methods

Isolation of Primary T Cells from Human Whole Blood and Expansion

Unless otherwise noted, all reagents were purchased from STEMCELL Technologies, Vancouver, Canada. Also, unless otherwise noted, all biologicals are human derived or human-specific.

Lyophilized human IL-2 ("IL-2") (Peprotech Inc., Montreal, Canada) was reconstituted to a concentration of 0.1 mg/ml in sterile 1×PBS without calcium or magnesium in a biological safety cabinet. Adding 50 µl of this IL-2 to 50 mL of ImmunoCult-XF™ T Cell Expansion Medium generated the medium for T cells. 7-30 mL of Human Whole Peripheral Blood with ACDA anticoagulant was placed in a sterile 50 mL polypropylene conical tube in a biological safety cabinet.

T cells were isolated from blood samples using an EasySep™ Direct Human T Cell Isolation Kit. First 50 µl/mL of Isolation Cocktail™ and then 50 µl/mL of the EasySep™ RapidSpheres™ were added to the tube of blood, which was mixed gently and incubated at Room Temperature (RT) for 5 minutes. The tube was placed into an EasySep™ 50 Magnet™ apparatus and incubated at RT for 10 minutes. The enriched cell suspension was pipetted into a new sterile 50 mL polypropylene tube, and the RapidSpheres™ process repeated.

This doubly enriched cell suspension was pipetted into a new sterile 50 ml polypropylene conical tube and centrifuged for 10 min at 300 g at RT. Supernatant was removed and the cell pellet was resuspended in 10 mL of PBS and respun at 300 g for 10 min to wash any remaining supernatant from the cells. The supernatant was again removed, and the cells resuspended in pre-warmed complete T cell media. A sample was drawn, and a Trypan blue exclusion test of cell viability was performed (Thermo Fisher).

Activation of T Cells Following Negative Selection Protocol

Blood was drawn from healthy human donors and combined with ACDA, an anticoagulant. A pan T cell negative selection kit, EasySep™ Direct human T cell isolation kit was used to isolate both CD4+ and CD8+ T cells. The cells were maintained in ImmunoCult-XF™ T Cell Exp Medium supplemented with IL-2. On the day of isolation, the cells were activated with a triple activator, ImmunoCult™ Human CD3/CD28/CD2 T Cell Activator.

Activation of T Cells Following Positive Selection Protocol

Blood was drawn from healthy human donors and combined with ACDA, an anticoagulant. A PBMC suspension was prepared using Lymphoprep™ density gradient centrifugation. T cells were then positively selected from the PBMC suspension using EasySep™ Human CD3 Pos Selection Kit II. The cells expressed IL-2. On the day of isolation, the cells were activated with a triple activator, ImmunoCult™ Human CD3/CD28/CD2 T Cell Activator.

Freezing and Thawing of T Cells

Blood drawn from healthy human donors was combined with ACDA, an anticoagulant. A pan T cell negative selection kit, EasySep™ Direct human T cell isolation kit was used to isolate both $CD4^+$ and $CD8^+$ T cells. Cells were cryopreserved using CryoStor® CS10 and stored in Liquid nitrogen. At the time of thaw, cells were maintained in ImmunoCult-XF™ T Cell Exp Medium supplemented with human recombinant IL2 (Peprotech). On the day of thaw, the cells were activated with either a double or a triple activator as indicated in the examples below.

Activation/Expansion of T Cells Detail

A T cell suspension was diluted in Complete T Cell media (ThermoFisher) to $10^6$ cells/ml, and the cells activated by adding 25 µl of either ImmunoCult™ Human CD3/CD28 (dual) T Cell Activator™ or Immunocult™ Human CD3/CD28/CD2 (triple) T Cell Activator™ per ml of T cell media. Cell growth was monitored by a daily cell count under magnification. Cells were diluted with Complete T Cell media to maintain concentrations of about $10^6$ cells/ml. On about day 5, 6 or 7, the T cells entered log phase of growth, and a rapid expansion occurred. FIG. 1 illustrates a T Cell expansion response over 10 days.

To confirm that the T cells are in log phase, CD25 expression was measured and had to be greater than 80% as assessed by flow cytometry (BD Biosciences), and the expansion of the cells can also be monitored by graphing the total number of T cells over time as in FIG. 1.

Microfluidic Mixing of Nucleic Acid Therapeutics (NAT) into Lipid Nanoparticles (LNP) to Form Lipid Nucleic Acid Particles (LNAP):

Lipid Mix composition solutions were prepared in ethanol by combining prescribed amounts of lipids (see Table 1) from individual lipid stocks in ethanol. The lipids were either purchased from Avanti Polar Lipids or Sigma, or contract synthesized. Components of the Lipid Mixes were as follows:

1,17-bis(2-octylcyclopropyl)heptadecan-9-yl 4-(dimethylamino)butanoate (with or without) hydrochloride (BOCHD-C3-DMA), neutral lipid DOPE, cholesterol and stabilizing agent Myrj52 (Polyoxyethylene (40) stearate) were components of Lipid Mix A.DODMA was used in place of BOCHD-C3-DMA for Lipid Mix A-DODMA, Dlin-Mc3-DMA for Lipid Mix A-MC3, and Dlin-KC2-DMA for Lipid Mix A-KC2. The ratios of neutral lipid, cholesterol, and stabilizing agents in all compositions are listed in Table 1, and in some cases, 0-0.1 Mol % of DiD label was added to the composition for post preparation lipid particle characterization. This mixture is the lipid mix solution referred to below.

For ionizable lipids, the pH of the nanoparticle formulation buffer is typically below the pKa of the lipid. Once formulated, the nanoparticles can be suspended in any physiologically relevant buffer such as PBS, Dextrose etc.

Messenger RNA or plasmid nucleic acid therapeutic (NAT) as described below, was diluted using sodium acetate buffer to the required concentration. Lipid nucleic acid particle (LNAP) samples were then prepared by running both fluids using the NanoAssemblr® Spark instrument. Briefly, 10-20 µg of nucleic acids in 100 mM sodium acetate buffer in a total volume of 32 µL was mixed with 16 µL of 37.5 mM lipid mix solution as required by the N/P ratios (4, 6, 8, 10 or 12 in illustrated examples). The microfluidically mixed lipid nucleic acid particles (LNAP) made in the instrument were immediately diluted down with 48 µL Ca++ and Mg++ free 1×PBS at pH 7.4 in the aqueous output well. These LNAP were immediately collected into microcentrifuge tubes containing 96 µL of the same buffer at pH 7.4. Encapsulation efficiency was measured by a modified Ribogreen™ assay (Quanti-iT RiboGreen™ RNA assay kit, Fisher). This information was used to established the desired dosage.

The nucleic acid therapeutic model reagents used in the following experiments were:

Trilink Cleancap eGFP mRNA: Cat. L-7601 (Trilink Biotechnologies, San Diego, CA); Trilink Cleancap EPO mRNA: Cat. L-7209 (Trilink Biotechnologies); Millipore Sigma TagRFP Simplicon RNA Kit: Cat. SCR712 (contains both TagRFP RNA & B18R RNA) (Millipore Sigma Canada, Oakville Ontario); CD19 CAR plasmid with EGFP reporter was purchased from Creative Biolabs (Shirley, NY) and contains a T7 promoter (Mut)-signal peptide-scFv-CD8 hinge transmembrane-4-1 BB-CD3zeta-T2A-eG FP reporter gene CAR cassette (2353 bp) within the pcDNA. The total size of this custom CD19 CAR plasmid DNA template is around 7649-7661 bp (see FIG. 26).

An unmodified CAR messenger RNA (mRNA) transcript encoding the CD19 scFv-h (BB±-eGFP reporter gene cassette was synthesized by in vitro transcription with wild-type bases and capped (Cap 1) using CleanCap® AG methodology by Trilink Biotechnologies Inc. This unmodified CAR mRNA transcript was enzymatically polyadenylated followed by a DNase and Phosphatase treatment. The final mRNA transcript product was silica membrane purified and packaged in a solution of 1 mM Sodium Citrate buffer (pH 6.4) at concentration of 1 mg/mL. This custom CD19 CAR plasmid vector and CD19 CAR encoding mRNA were purchased from Creative Biolab and Trilink Biotechnologies Inc respectively.

"IL" is ionizable lipid. Where not specified, the ionizable lipid is BOCHD-C3-DMA. In other cases, as marked or noted in the figure descriptions, the ionizable lipid is DODMA, Dlin-Mc3-DMA, or Olin-KC2-DMA as marked in the Examples and Figures.

TABLE 1

Components and Ratios of Lipid Mixes

| Name | Components, Units are Mole %, Ionizable Lipid/structural lipid/cholesterol/surfactant |
|---|---|
| Lipid mix A | 50/10 DSPC/37.5/2.5 Myrj52 (Polyoxyethylene (40) stearate) |
| Lipid mix S8 | 50/10 DSPC/37.5/2.5 BRIJ ™ 35 (Polyoxyethylene lauryl ether) |
| Lipid mix S9 | 50/10 DSPC/37.5/2.5 BRIJ ™ S20 (Polyoxyethylene (20) stearyl ether) |
| Lipid mix S10 | 50/10 DSPC/37.5/2.5 TPGS1000 |
| Lipid mix S11 | 50/10 DSPC/37.5/2.5 BRIJ ™ S10 (Polyoxyethylene (10) stearyl ether) |
| Lipid mix S12 | 50/10 DSPC/37.5/2.5 BRIJ ™ L4 (Polyoxyethylene (4) lauryl ether) |
| Lipid mix LM02 | 50/10 DSPC/38.5/1.5 PEG-DMG-2K |
| Lipid mix CT7 | 50/10 DSPC/38.5/1.5 polysorbate 80 |
| Lipid mix CT8 | 50/10 DSPC/39.5/0.5 Myrj52 (Polyoxyethylene (40) stearate) |
| Lipid mix CT10 | 40/20 DSPC/37.5/2.5 BRIJ ™ S10 (Polyoxyethylene (10) stearyl ether) |
| Lipid mix CT22 | 40/20 DSPC/38.5/1.5 polysorbate 80 |
| Lipid mix CT14 | 40/20 DSPC/39.5/0.5 TPGS 1000 (D-α-Tocopherol polyethylene glycol 1000 succinate) |
| Lipid mix CT34 | 40 Mol % ionizable lipid, 20 Mol % DSPC, 39.5 Mol % cholesterol, 0.5 Mol % Brij ™ 20 |

Lipid based formulations were also manufactured using the larger NanoAssemblr® Benchtop (later released as "Ignite" with advanced features but similar volumes) for testing. Briefly, 350 μL of 1 mg/ml mRNA or pDNA was diluted using 100 mM sodium acetate buffer (pH 4) to the required concentration of 0.05 to 0.3 mg/ml depending on N/P ratio of 12, 10, 8, 6 or 4. Lipid nanoparticle samples were then prepared by running both fluids, namely, nucleic acids in aqueous solvent and Lipid Mix in ethanol at a flow ratio of 3:1 and at a total flow rate of 12 ml/minute. Following mixing in the microfluidic device, the post cartridge lipid nucleic acid particle sample was diluted into RNAse free tubes containing three to 40 volumes of phosphate buffered saline (PBS) buffer, pH 7.4. Ethanol was finally removed using Amicon™ centrifugal filters (Millipore, USA) at 3000 RPM, or using TFF systems. Once the required concentration was achieved, the lipid nucleic acid particles were filter sterilized using 200 μm filters in aseptic conditions. Final encapsulation efficiency was measured by a modified Ribogreen™ assay.

After the lipid particles were made as described in above, particle size (hydrodynamic diameter of the particles) was determined by Dynamic Light Scattering (DLS) using a ZetaSizer Nano ZS™, Malvern Instruments, UK). He/Ne laser of 633 nm wavelength was used as the light source. Data were measured from the scattered intensity data conducted in backscattering detection mode (measurement angle=173). Measurements were an average of 10 runs of two cycles each per sample. Z-Average size was reported as the particle size, and defined as the harmonic intensity averaged particle diameter. Particle size measurements were also done using Zetasizer Ultra (Malvern Instruments, UK) using multi angle dynamic light scattering.

The results of the nucleic acid encapsulation for various Lipid Mixes described in the application are shown in Table 2. Observed particle attributes were generally in the range of 68-122 nm for mRNA or SARNA, and 73-153 nm for plasmid. There was good encapsulation in all the formulations, with size variation or polydispersity (POI) under 0.3.

TABLE 2

Physicochemical Properties of Nucleic Acid LNPs Manufactured on the NanoAssemblr® Spark, Benchtop, and Benchtop later model "Ignite ™"

| ID | AVG Size | AVG PDI | EE % |
|---|---|---|---|
| Spark LNP | | | |
| Lipid Mix A mRNA | 93.0 | 0.26 | 97.7 |
| Lipid Mix S10 mRNA | 110.4 | 0.12 | 89.8 |
| Lipid Mix S11 mRNA | 107.3 | 0.11 | 93.8 |
| Lipid Mix CT10 mRNA | 112.6 | 0.08 | 93.2 |
| Lipid Mix CT7 mRNA | 121.6 | 0.09 | 72.6 |
| Lipid Mix CT22 mRNA | 119.1 | 0.08 | 58.0 |
| Lipid Mix A Plasmid | 125.8 | 0.26 | 98.5 |
| Lipid Mix S11 Plasmid | 91.2 | 0.21 | 92.3 |
| Lipid Mix CT10 Plasmid | 72.7 | 0.26 | 70.4 |
| Lipid Mix CT7 Plasmid | 152.6 | 0.12 | 55.6 |
| NABT LNP | | | |
| Lipid Mix A mRNA | 68.0 | 0.07 | 84.7 |
| Lipid Mix CT10 mRNA | 71.7 | 0.09 | 90.6 |
| Lipid Mix CT22 mRNA | 89.1 | 0.08 | 74.3 |
| Lipid Mix A Plasmid | 101.0 | 0.12 | 95.0 |
| Ignite LNP (later model of NABT) | | | |
| Lipid Mix CT10 Plasmid | 85.0 | 0.07 | 72.8 |
| Lipid Mix A Simplicon TagRFP Self-Replicating RNA | 85.4 | 0.11 | 91.8 |
| Lipid Mix A B18R RNA | 67.6 | 0.13 | 94.6 |
| Lipid Mix CT10 Simplicon TagRFP Self-Replicating RNA | 61.8 | 0.16 | 96.6 |
| Lipid Mix CT10 B18R RNA | 79.2 | 0.11 | 95.4 |

Example 1

All reagents from StemCell Technologies unless otherwise stated. T cells were isolated from whole human peripheral blood using a negative selection isolation procedure (EasySep™ Human T Cell Isolation Kit). T cell activation and expansion was carried out using Immunocult™ Human CD3/CD28/CD2 Activator in ImmunoCult™ Human T Cell Expansion Media supplemented with recombinant human IL-2 (Peprotech Inc., Rocky Hill USA). A representation of a typical T cell growth curve is provided in FIG. 1. T cells typically enter a logarithmic phase of growth 48-96 hours after activation, which phase is characterized by a period of rapid proliferation and metabolic activity for 24-72 hours followed by a plateau in the growth curve as the cells start to return to a quiescent state. As depicted in FIG. 1, T cells may be exposed to lipid nucleic acid before or during the log phase of growth (day 3), or after the log phase of growth (day 7).

We tested the compositions of new Lipid Mixes against standard Lipid Mix A (all with BOCHD-C3-DMA as IL unless otherwise stated) using the triple T cell activation protocol (Pan T cells were activated with trio activator comprising anti-CD3/CD28/CD2 antibody) in LNP-mediated mRNA delivery and expression in vitro.

LNP formulated EGFP mRNA (Trilink Biotechnologies, San Diego, CA) was added to 500,000 T cells in 1 ml of complete T cell media, with 1 μg/ml of Recombinant Human ApoE4 ("ApoE") (Peprotech Inc.).

The volume of LNAP required to achieve the desired dose of mRNA was calculated based on the concentration of encapsulated mRNA as determined by modified Ribogreen™ assay. T cells were counted through Trypan blue (Sigma) exclusion and diluted to 500,000 cells/mL. Briefly, in a 12 well plate, 1 mL was aliquoted into each well. ApoE was added to a final concentration of 1 μg/mL in each well. Based upon the calculation in step 1, the required amount of mRNA LNP was added, in this case 2 μg, and the plate incubated for 48 hours.

Figure 2:
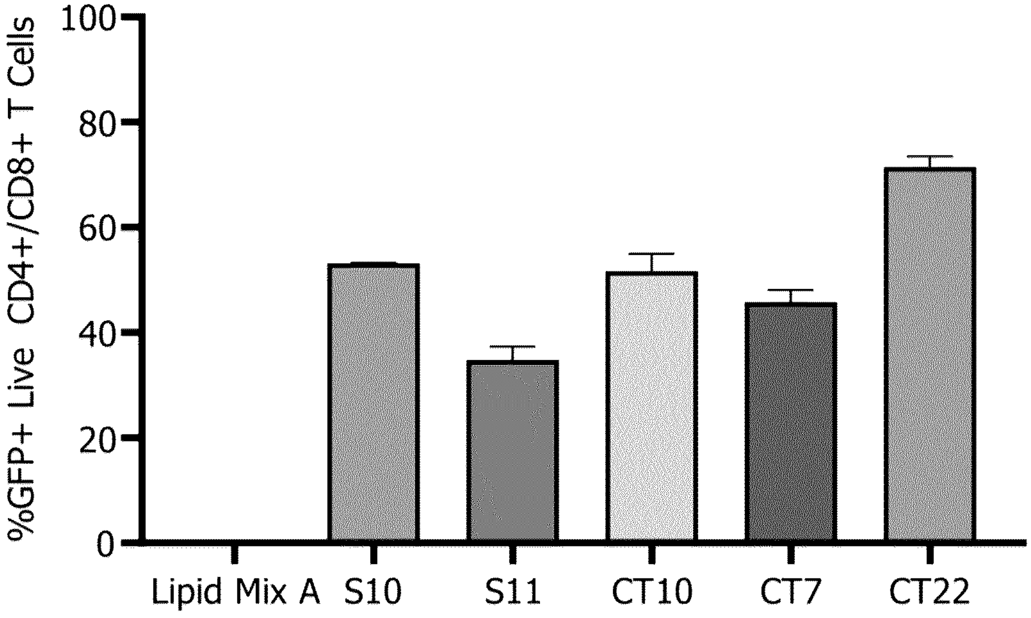
FIG. 2 is a bar graph showing relative GFP protein expression in live CD4+/CD8+ T cells treated 7 days post activation with 2 μg of mRNA per 500,000 cells in BOCHD-C3-DMA LNPs of six different lipid mix compositions exposed for 48 h.
Figure 3:
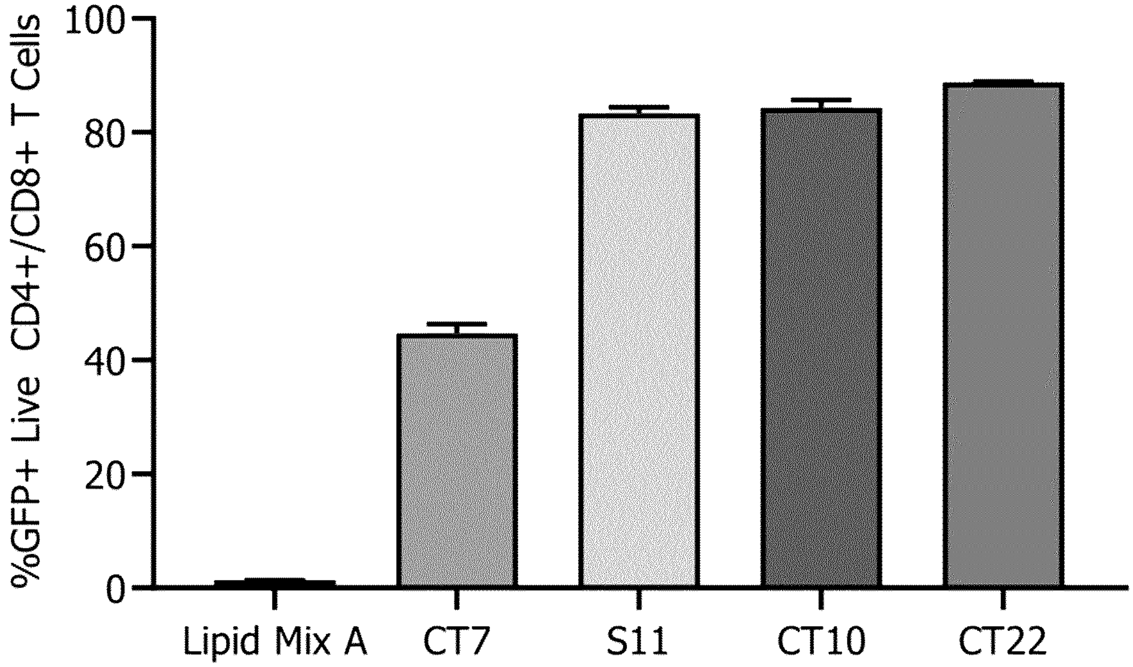
FIG. 3 is a bar graph showing relative GFP protein expression in live CD4+/CD8+ T cells treated 7 days post activation with 2 μg of mRNA per 500,000 cells in MC3 LNPs of five different lipid mix compositions exposed for 48 h.

Different lipid mix compositions were tested for their ability to induce transfection as measured by geometric mean fluorescence intensity of GFP expressed in T cells (as measured by flow cytometry). FIG. 2 shows the increased effect of different LNP compositions S10, S11, CT10, CT7, and CT22 composition (details in Table 1) using the ionizable lipid BOCHD-C3-DMA at an N/P ratio 10 as compared to Lipid Mix A. FIG. 3 shows the effect on the % GFP positive live $CD4^+/CD8^+$ T cells of different LNP compositions CT7, S11, CT10, and CT22 using the ionizable lipid MC3 at N/P ratio 10. Lipid mixes CT7, S11, CT10, and CT22 gave a higher level of transfection than Lipid Mix A.

Figure 4:
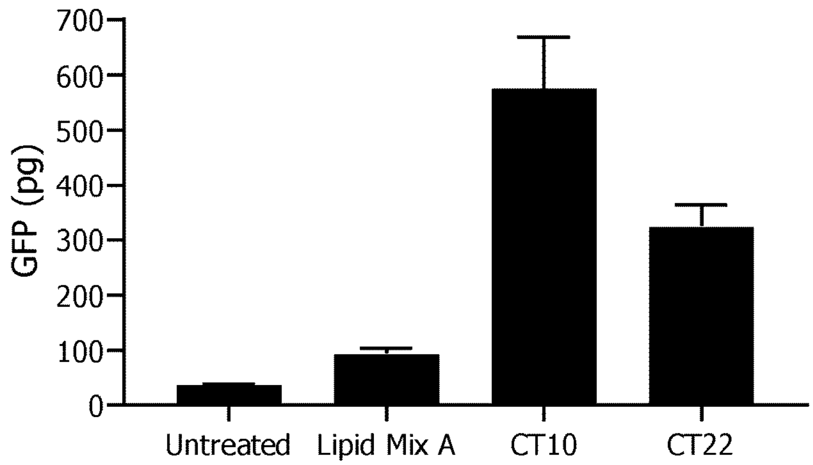
FIG. 4 is a bar graph showing total GFP expression in negatively selected T cells mediated by mRNA Lipid Nanoparticles (LNP) formulated with CT10, CT22 and Lipid Mix A composition, and analyzed for gene expression by ELISA. The ionizable lipid was BOCHD-C3-DMA for all three compositions.

When the GFP expression was measured quantitatively, in picograms, the results are shown in FIG. 4. CT10 and CT22 perform much better than Lipid Mix A.

Figure 5:
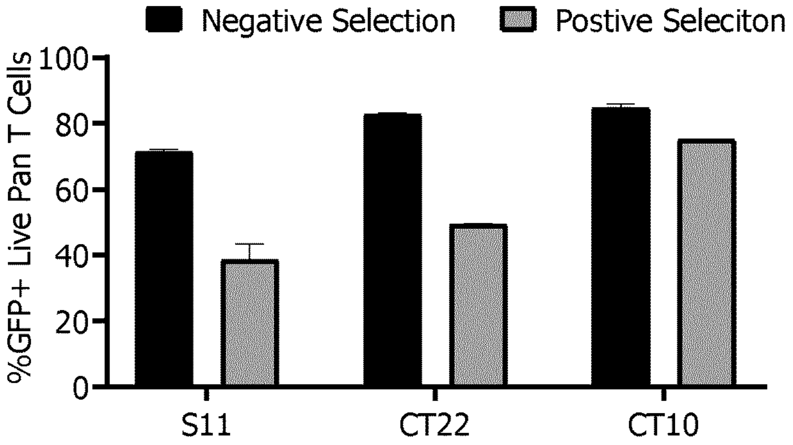
FIG. 5 is a distribution plot for GFP expression in mRNA-treated T-cells from different donors of both sexes aged 20-75 years. Different shape and/or pattern of the data point represents different donors, each of which cell population was tested with 5 different lipid mix compositions Lipid Mix A, CT7, S11, CT10, CT22.

The relative effect of Lipid Mix A, S11, CT7, CT10 and and CT22 formulations on T cells from a number of human donors aged 20-75 years of both genders was compared to examine subject-to-subject variability. FIG. 5 is a distribution plot for GFP expression in mRNA-treated T cells from different donors. Exposure to the lipid mix compositions occurred on day 7 after activation, near the end or just after the log phase of growth. Across the formulations tested, inherent donor variability appeared to influence formulation performance, however, donors with low performance in one Lipid Mix generally had lowered performance across all Lipid Mixes. All compositions, CT7, S11, CT10, and CT22 had better performance compared to lipid mix A across all donors. Some formulations, for example CT10 or CT22, appeared more robust in their ability to consistently achieve high transfection efficiency.

Table 3 below shows the geometric mean fluorescence intensity (MFI) for different lipid mix compositions. MFI is arguably a more precise measurement than % GFP expressing cells. The MFI shown below describes the level of eGFP produced by delivered mRNA. The triple activated T cells transfected on day 7 with Lipid Mix A LNAP and LMO2 LNAP gave a low MFI score, indicating poor success in transfection and expression. Those transfected with S10 showed an MFI score of 6. The best lipid mix compositions were S11, CT7, CT10, and CT22, all with scores of 10. The data shows that LNAPs made using stabilizing agents such as TPGS1000, Brj S10, and Tween 80 induced surprisingly higher eGFP protein than stabilizing agent Myrj52, or even industry standard PEG-DMG-2K.

TABLE 3

Mean Fluorescent Intensity Achieved by Lipid Mix Compositions Formulated with mRNA using BOCHD-C3-DMA as the Ionizable Lipid.

| Composition ID | Surfactant used | MFI Score (fold increase over Lipid Mix A) |
|---|---|---|
| Lipid Mix A | Myrj52 | 1 |
| S10 | TPGS1000 | 6 |
| S11 | Brij S10 | 10 |
| LM02 | Lipid PEG-DMG | 2 |
| CT7 | Tween80 | 10 |
| CT10 | Brij S10 | 10 |
| CT22 | Tween 80 | 10 |

The results for both MC3 and BOCHD-C3-DMA were comparable. Results were consistent with those attained using the dual activation protocol which uses anti-CD3/CD28 antibodies.

Example 2

Effect of Negative and Positive Selection Protocol on T Cell Transfection

Figure 6:
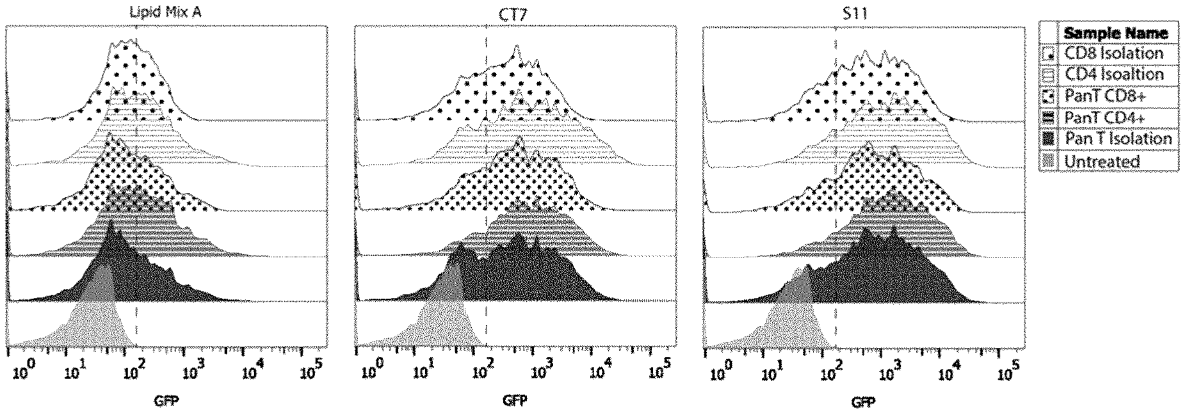
FIG. 6 is a bar graph showing relative GFP expression in live T cells mediated by mRNA in BOCHD-C3-DMA LNPs at a dose of 2 μg mRNA per 500,000 cells and at a N/P ratio of 10. Primary human T cells from the same donor were isolated from fresh whole blood using either negative selection or positive selection protocol and activated using a triple activator.

T cells were processed by either Negative Selection or Positive Selection protocols as described in the Methods above, and treated with CT10, CT22 and S11 Lipid Mix Compositions formulating mRNA on day 7 at a dose of 2 μg mRNA per 500,000 cells at N/P 10. T cells were analyzed for gene expression by flow cytometry 48 hours after treatment. We found that LNAP transfection success is not substantially affected by the T cell isolation process, although we observed a slight advantage in using negative selection (FIG. 6).

Example 3

Downstream Processing and Analysis of Treated T Cells with Flow Cytometry

Three isolations of T cells were taken from a single donor and divided into three groups: Pan T cells (all T cells), CD4+ T cells alone, and CD8+ T cells alone. At 48H following lipid particle mRNA exposure, the treated T cells were harvested by transferring the cell suspensions to pre-labeled 1.5 mL tubes and centrifuged 300×g at 4 degrees Celsius for 10 minutes. Supernatant was removed and the pellet resuspended in PBS. An amount of 0.5 ul of BD Horizon™ Fixable Viability Stain 575V™ (BD Biosciences) was added, and the mixture incubated in the dark for 10 minutes at RT. The cells were centrifuged again as before, then washed twice with 1 ml of Stain buffer (BSA, BD Pharminigen), and the washed pellet placed in 100 μl BSA. The following antibodies were added to each tube of treated cells in 2 μl volumes: anit-D025, anti-CDB, anti-C04, (PerCP-Cy 5.5 Mouse Anti Human C025, BV786 Mouse Anti-Human CD8 Clone RPA-T8, and APC-Cy™7 Mouse Anti-Human C04 Clone SK3, all from BD Pharmingen). For compensation purposes, in the GFP only sample and viability control, no antibody was added, while in the single stain compensation tubes, only one antibody was added.

The tubes were incubated at 4 degrees C. for 30 min, whereupon 400 μl of stain buffer (BSA) was added, and the cells were centrifuged again. Cells were washed once with 1 mL of stain buffer and spun down again as in step 1. Cell pellets were resuspended in 1 mL of stain buffer and added to pre-labeled flow tubes with cell strainer caps (Corning Falcon).

Figure 7:
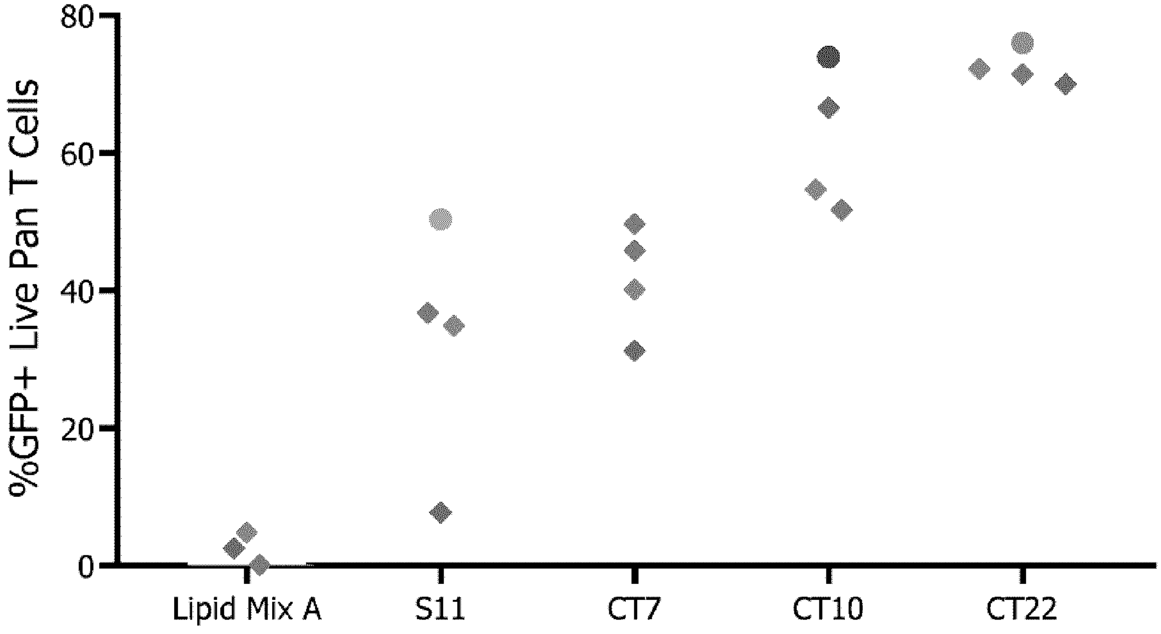
FIG. 7 is a histogram showing cell populations having certain characteristics as measured by flow cytometry of live primary human T cells treated 7 days post activation with mRNA LNPs of three different lipid mix compositions for 48 h. From top to bottom, the histograms represent GFP expression from cells from the CD8+ isolation (large polka dots), CD4+ isolation (horizontal pale stripe), Pan T isolation CD8+ cells only (smaller polka dots), Pan T isolation CD4+ cells only (horizontal dark stripe), all T cells from the Pan T isolation (dark grey), and finally untreated cells (light translucent grey). The ionizable lipid was BOCHD-C3-DMA.

Histogram Analysis of T Cell Populations was generated as follows: Flow cytometry was performed on the live primary human T cells. As illustrated in FIG. 7, from top to bottom, the histograms represent GFP expression from cells from the CD8$^+$ isolation, CD4$^+$ isolation, Pan T isolation CD8$^+$ cells only, Pan T isolation CD4$^+$ cells only, all T cells from the Pan T isolation, and untreated cells. The left lane shows GFP expression using Lipid Mix A, the middle lane shows GFP expression using Lipid Mix CT7, and the far right lane shows GFP expression using Lipid Mix S11. All LNP compositions contained BOCHO-C3-DMA as ionizable lipid (IL). For the gating of each population, cells were first gated by forward and side scatter followed by exclusion of doublets, and only live cells were considered through use of Fixable Viability Stain 570 (BD Biosciences). Cells were stained with CD4 and CD8 antibodies, which allowed for gating of each subpopulation. FIG. 7 shows that the untreated cells are neutral while the treated T cells various labels show a raised and consistent GFP expression.

Example 4

Activity Depends on Precise Lipid Mix Composition for T Cells—Structural Lipid

Figure 8:
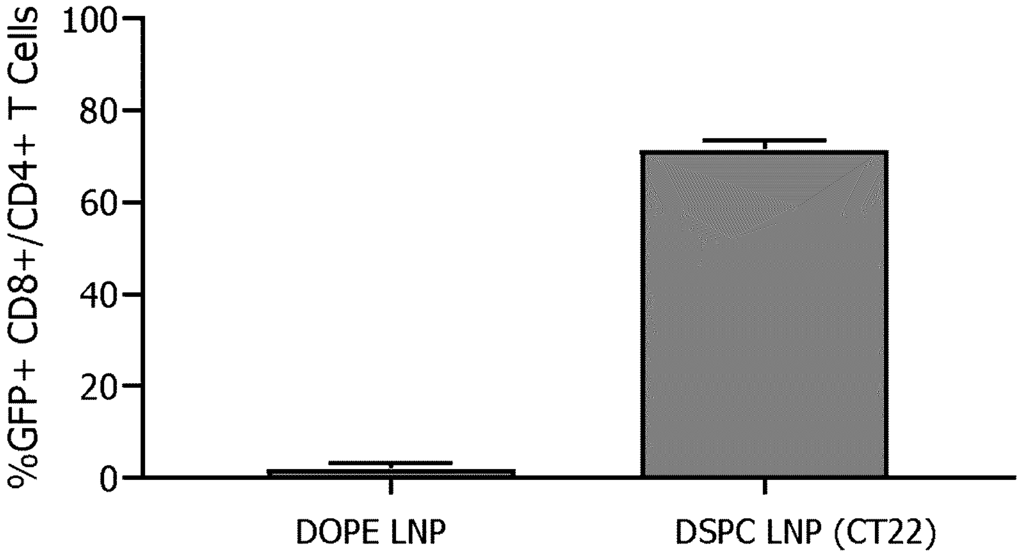
FIG. 8 is a bar graph showing relative GFP protein expression derived from LNAP treated live CD4+/CD8+ T cells. The first bar labelled DOPE LNAP contains structural lipid DOPE in place of DSPC, while the second bar labeled DSPC LNAP (CT22) has DSPC as the structural lipid. Both lipid mix compositions correspond to Lipid Mix CT22 in terms of proportions of IL, structural lipids, cholesterol and polysorbate 80.

Studies were undertaken to test lipid mix compositions of different components. Generally, T cells were isolated from human peripheral blood cells using a negative selection procedure. On the day of isolation, the cells were activated with a triple activator. FIG. 8 is a bar graph showing relative GFP protein expression in live CD4$^+$/CD8+T cells treated 7 days post activation with eGFP mRNA in BOCHD-C3-DMA (N/P 10) LNPs for 48 Hours at a dose of 2 μg of mRNA per 500,000 cells. Lipid Mix CT22 ratios of components were used, but the structural lipid was either DOPE or DSPC.

Earlier studies in different cell types (such as neurons) showed a preference for DOPE as the structural lipid. However, we found structural lipid DSPC was better than DOPE for T cell transfection. Table 4 lists the components and ratios of the lipid mix compositions whose transfection efficiency was illustrated in FIG. 8.

TABLE 4

DOPE and DSPC as structural lipids in two similar formulations

| Description: | DOPE LNP | Lipid Mix CT22 |
|---|---|---|
| Figure Label: | DOPE LNP | DSPC LNP |
| IL | 40 Mol % | 40 Mol % |
| Structural Lipid | 20 Mol % DOPE | 20 Mole % DSPC |
| Cholesterol | 37.5 Mol % | 37.5 Mol % |
| Surfactant (Polysorbate 80) | 2.5 Mol % | 2.5 Mol % |

Example 5

Activity Depends on Precise Lipid Mix Composition for T Cells—Ratios

Figure 9:
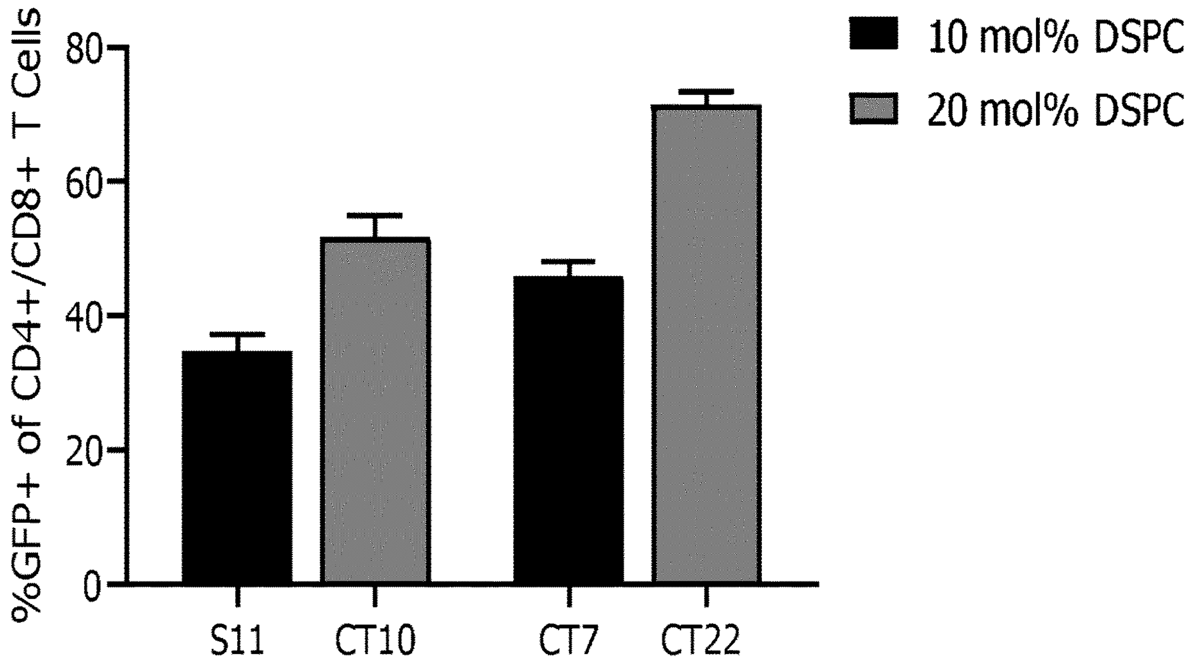
FIG. 9 is a bar graph showing the GFP expression in activated, transfected T cells by four different compositions with two different molar ratios of DSPC.

GFP expression in transfected T Cells was assayed as in Example 4 above. FIG. 9 is a bar graph showing the GFP expression in activated, transfected T cells for four different Lipid Mix compositions with either 10 Mol % (S11, CT7) or 20 Mol % (CT10, CT22) of DSPC. Twenty Mol % of DSPC was significantly better than the 10% ratio of DSPC in the tested compositions; from 20 to 30 percent difference in the amount of GFP expression was seen between the two ratios.

Figure 10:
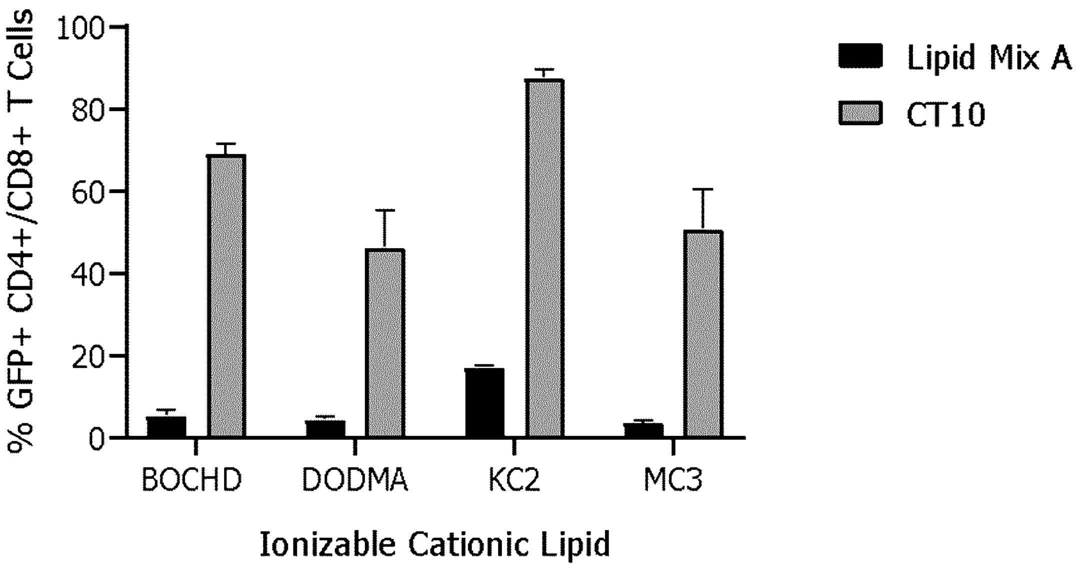
FIG. 10 is two bar graphs, the first showing relative GFP protein expression in live CD4+/CD8+ T cells treated 7 days post activation, with 2 μg of mRNA per 500,000 cells over 48 h, and wherein the ionizable lipid was one of BOCHD-C3-DMA, DODMA, KC2, or MC3. The second is a graphical representation of LNP-mediated transfection of isolated human T cells as measured by viability (black bars) and GFP expression (grey bars) using 500 ng LNAP per 125, 000 cells of CT10 composition with either BOCHD-C3-DMA or C12-200 as the ionizable lipid.
Figure 10:
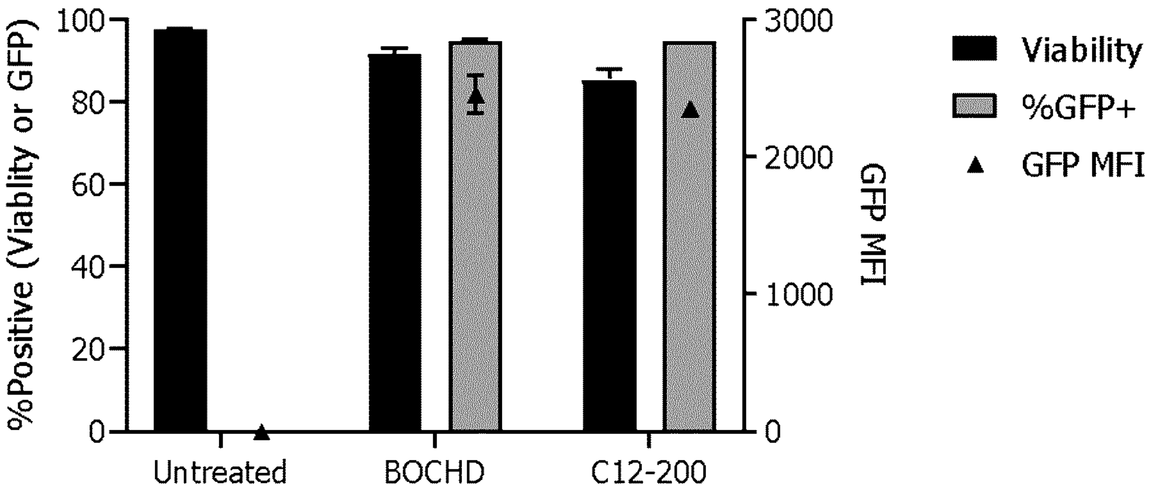

Another facet of the importance of the components selected is illustrated in FIG. 10. As illustrated in the upper bar graph, the identity of the ionizable lipid was shown not to have an effect on the activity of the lipid mix compositions. The same ratios and materials were combined while varying the identity of the ionizable lipid among MC-3, KC2, and BOCHD-C3-DMA. These ionizable lipids could be substituted for each other without affecting the activity of the lipid mix composition to transfect T cells.

Indeed, as shown in the lower bar graph, the lipidoid C12-200 as ionizable lipid gave similar results to BOCHD-C3-DMA in terms of viability, % GFP expressing T cells, and GFP MFI, when administered in a CT10 lipid mix composition.

In conclusion, under these conditions, the choice of structural lipid affected the transfection efficiency {% GFP+), but the choice of ionizable lipid did not appear to. This shows the surprising influence of specific structural lipids in LNP composition as a major influencing factor on activity as opposed to the ionizable lipid.

Example 6

Activity Depends on Precise Lipid Mix Composition for T Cells—Stabilizing Lipid

Isolation of primary T cells from human whole blood and activation/expansion was performed as in general procedures above. Isolated T cells were exposed to the formulated mRNA three days after activation; in the T cell growth curve, this time point corresponds to just before or at the log phase of growth. A dose of 125 ng of CleanCap™ EGFP (Trilink Biotechnologies, San Diego, CA) mRNA encapsulated in LNP {see details below) was added to about 125,000 T cells in 0.25 ml of complete T cell media, with 1 μg/ml of Recombinant Human ApoE4 ("ApoE") (Peprotech Inc., Montreal, Canada).

The volume of LNP required for T cell treatment was calculated based upon Ribogreen™ assay results. T cells were counted through Trypan blue (Sigma) exclusion and diluted to 500,000 cells/mL. Briefly, in a 48 well plate, 0.25 mL was aliquoted into each well. ApoE was added to a final concentration of 1 μg/mL in each well. Based upon the volume calculation, the required amount of mRNA LNP was added, and the plate incubated for 48 hours.

Lipid mix compositions were tested for their ability to induce transfection, using flow cytometry to measure the geometric mean fluorescence intensity of eGFP. Shown in FIG. 11 A(i) to D(ii) are the transfection efficiencies (i) and mean fluorescence intensities (ii) of mRNA LNPs encoding eGFP in isolated primary human T cells under various conditions. The lipid mix composition is defined as ionizable lipid 40 Mol %, DSPC 20 Mol %, cholesterol 40-x Mol %, stabilizer x Mol %, where x=0.5, 1.5, or 2.5 Mol %.

Figure 11:
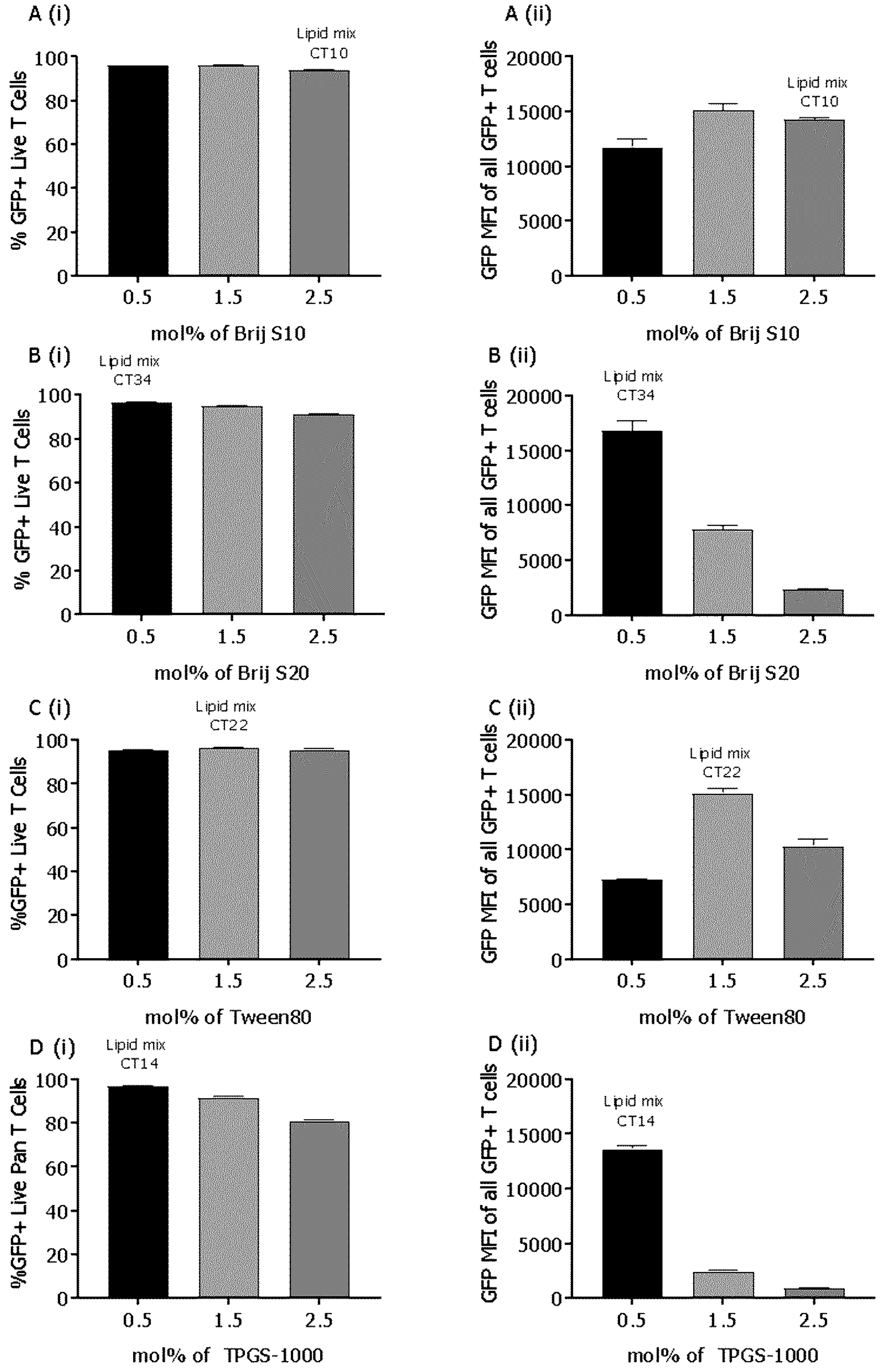
FIG. 11 is a series of bar graphs showing results for the lipid mix composition comprising 40 Mol % ionizable lipid, 20 Mol % DSPC, 40-x Mol % cholesterol, and x Mol % stabilizer, where x=0.5, 1.5, or 2.5 Mol %; Bar graphs labeled A(i) and (ii) are transfection efficiency, (i) and MFI (ii) of mRNA LNPs encoding eGFP in isolated primary human T cells with stabilizer Brij S10; bar graphs B(i) and (ii) are transfection efficiency (i) and MFI ii) with stabilizer Brij S20; bar graphs C(i) and (ii) are transfection efficiency (i) and MFI (ii) with stabilizer Tween80; and bar graphs D(i) and (ii) are transfection efficiency (i) and MFI (ii) with stabilizer TPGS-1000 (D-α-Tocopherol polyethylene glycol 1000 succinate)

The identity of the stabilizer as varied in FIG. 11, graphs A-D were as follows: Fig. A(i) and (ii) are data attained with stabilizer Brij S10, B(i) and (ii) are data attained with stabilizer Brij S20, C(i) and (ii) are data attained with stabilizer Tween80, and D(i) and (ii) are data attained with stabilizer TPGS-1000. The ionizable lipid used in all cases is BOCHD-C3-DMA. The T cells were isolated and activated using a triple activator on day 0, exposed to formulated mRNA on day 3, and harvested for flow cytometry on day 5.

It was found that exposing the cells to the mRNA LNPs three days after activation, corresponding to the very beginning of the log phase of growth, resulted in greater than 80% transfection efficiency for all compositions tested. It was also found that for each stabilizer used, the Mol % of stabilizer in the lipid mix composition influenced the total eGFP expression as indicated by the MFI. For each stabilizer, the Mol % which induced the maximal eGFP expression is indicated with the following names: Lipid Mix CT10, Lipid Mix CT34, Lipid Mix CT22, and Lipid Mix CT14.

As measured by MFI, for Brij S10, 1.5 Mol % was the best ratio; for Tween80, 1.5 Mol % was the best ratio. For Brij S20, 0.5 Mol % was the best ratio; and for TPGS-1 000, 0.5 Mol % was the best ratio.

Testing of nonionic surfactants with differing chain lengths indicates that shorter polyoxyethylene chains are better for T cell delivery ex vivo.

Example 7

Lipid Compositions Effect on Cell Viability.

Figure 12:
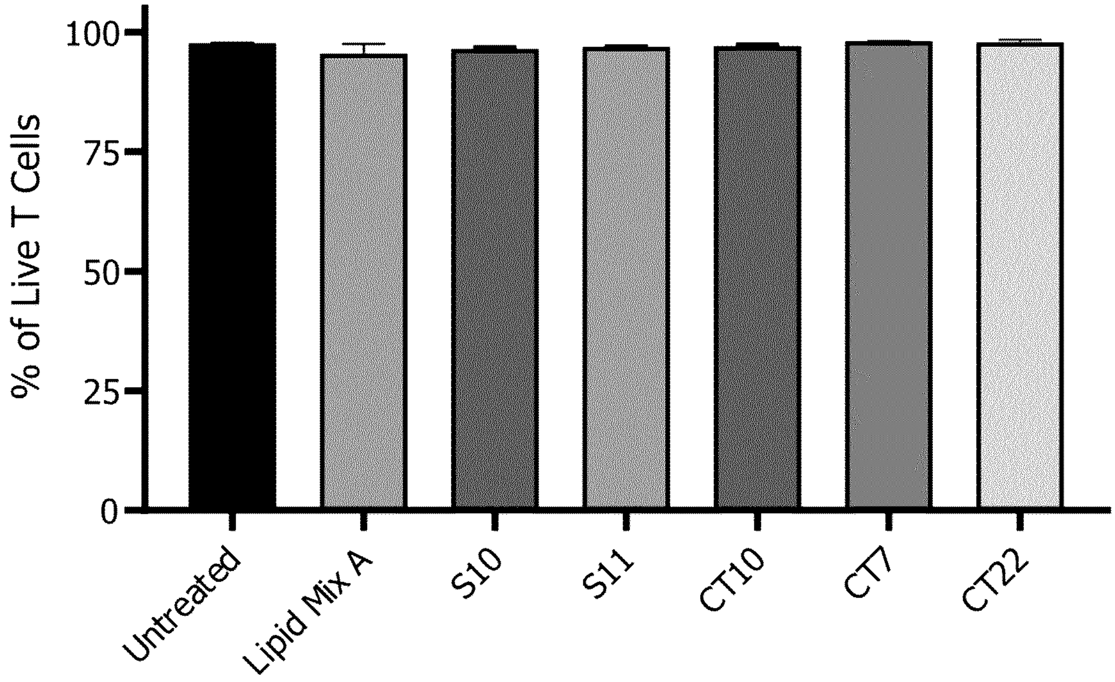
FIG. 12 is a bar graph showing viability of CD4+/CD8+ T cells treated 7 days post activation with mRNA LNPs at N/P 10, comprised of the lipid mix compositions referenced in the x axis, with live cells determined by flow cytometry using a live/dead stain FVS 570. The ionizable lipid was BOCHD-C3-DMA for all three compositions.

The effect on T cell viability exerted by treating T cells with nucleic acid containing Lipid composition Mixes during the sensitive Log Phase was investigated. T cells activated as in previous examples were treated during the Log Phase of growth. T cell viability post treatment is shown in the bar graph in FIG. 12. Lipid Mixes A, S10, S11, CT10, CT7, and CT22 had no negative effect on T cell viability as compared to a "no treatment" control. In a separate study not shown, we found that Transfectamine™ laboratory reagent was more toxic to these cells at similar doses.

Thus, one can treat during T cell expansion and there is no loss in proliferation.

Example 8

Figure 13:
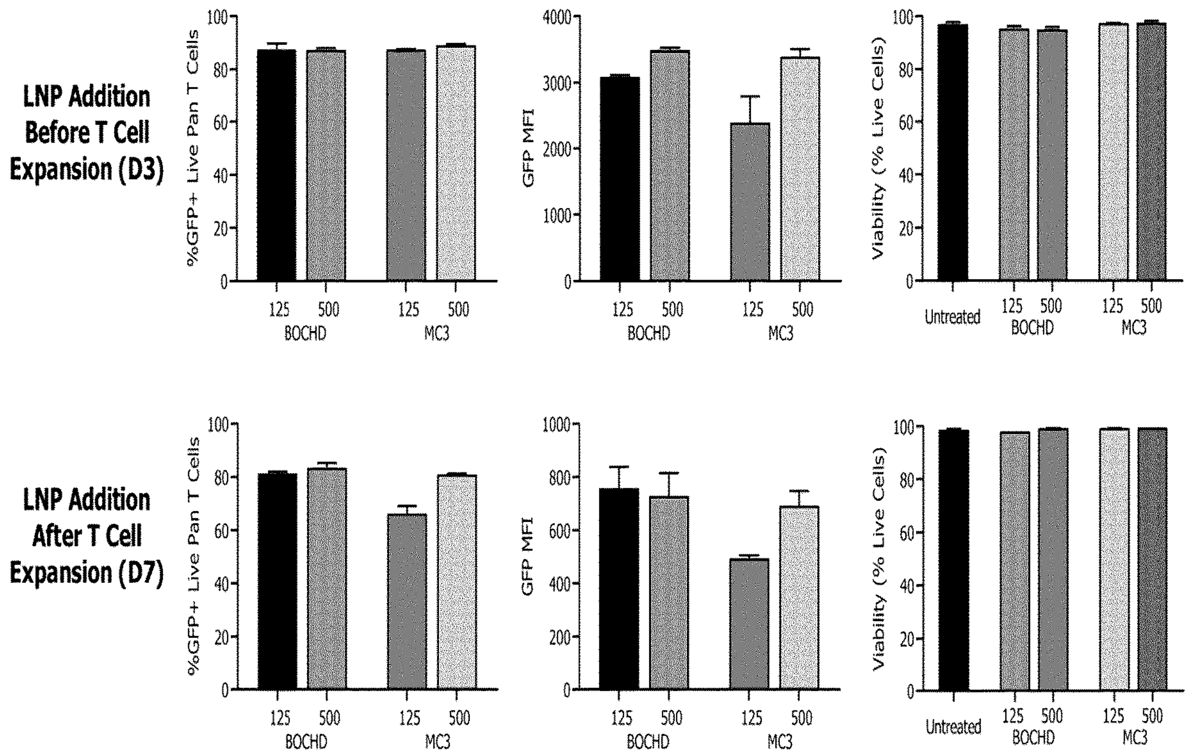
FIG. 13 is a series of bar graphs showing three measurements, namely % GFP+ live PAN T cells, GFP MFI, and T Cell viability, after T cells were exposed to CT10 LNAP either day 3 or day 7 after T cell expansion was initiated with either BOCHD-C3-DMA or MC3 as ionizable lipid.

Treatment of Activated T Cells with GFP mRNA LNPS—Effect of T Cell Activation State on Transfection GFP expression was assayed in isolated primary human T cells as prepared according to methods described above mediated by mRNA-LNPs containing lipid BOCHD-C3-DMA or MC3 in a CT10 composition at N/P 10. Transfection efficiency and geometric mean fluorescence intensity (MFI) were measured by flow cytometry 48 hours after LNAP addition. T cells were dosed with 125 or 500 ng of encapsulated mRNA LNPs per 125,000 cells either 3 or 7 days after activation, and results of the GFP assays are shown in FIG. 13. The assays demonstrate the ability of the CT10 composition LNAP to transfect T cells before, or after the activation phase, at two dosages and with two different ionizable lipids (BOCHD-C3-DMA and MC3). Percent GFP in live T cells and GFP MFI are shown and are slightly higher for the day 3 LNP addition. Note that the viability of the T cells remains high despite treatment in the third and sixth bar graph (Viability).

Example 9

Activity Maintained Over Different Donors

Figure 14:
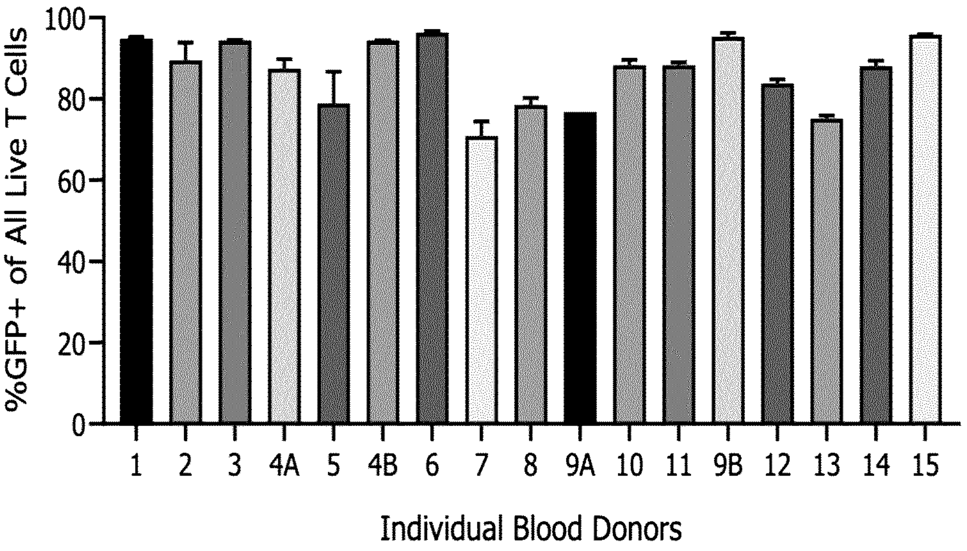
FIG. 14 is a graphical representation of GFP % expression in viable Pan T cells exposed to LNAP on day 3 after activation from 15 different donors using BOCHD-C3 as the ionizable lipid in CT10 composition.
Figure 15:
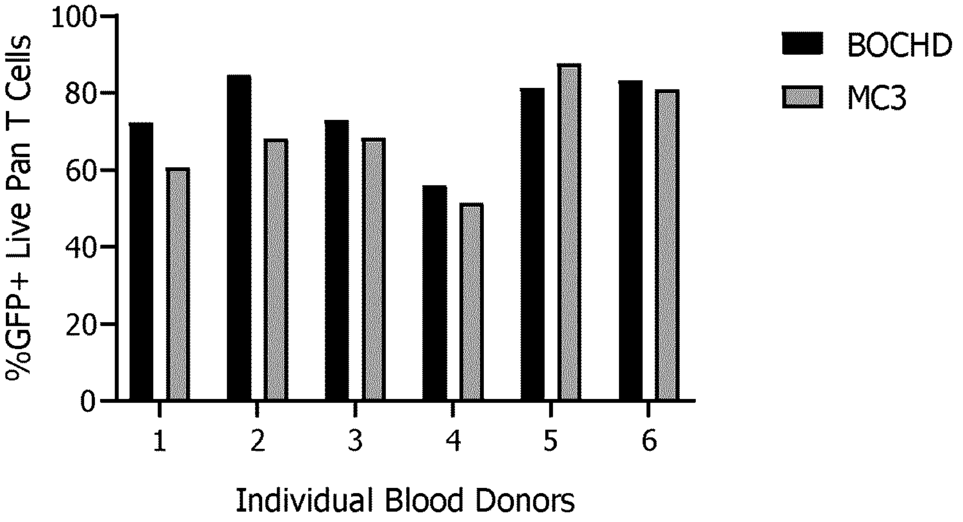
FIG. 15 is a graphical representation of GFP % expression in viable Pan T cells from 6 different donors exposed to LNAP on day 7 using BOCHD-C3 (black bars) or MC3 (grey bars) as the ionizable lipid in CT10 composition.

T cells isolated from 15 different donors were able to express GFP after treatment with CT10 mediated eGFP mRNA. The results of this study, shown in FIG. 14, demonstrate consistent success in transfecting many donors' T cells. In yet another study, industry standard MC3 was compared to BOCHD-C3-DMA in six different patients. As shown in FIG. 15, there appeared to be no substantial difference between the two different ionizable lipids in terms of donor to donor variability. This means that consistent results would be expected in human patients.

Example 10

Figure 16:
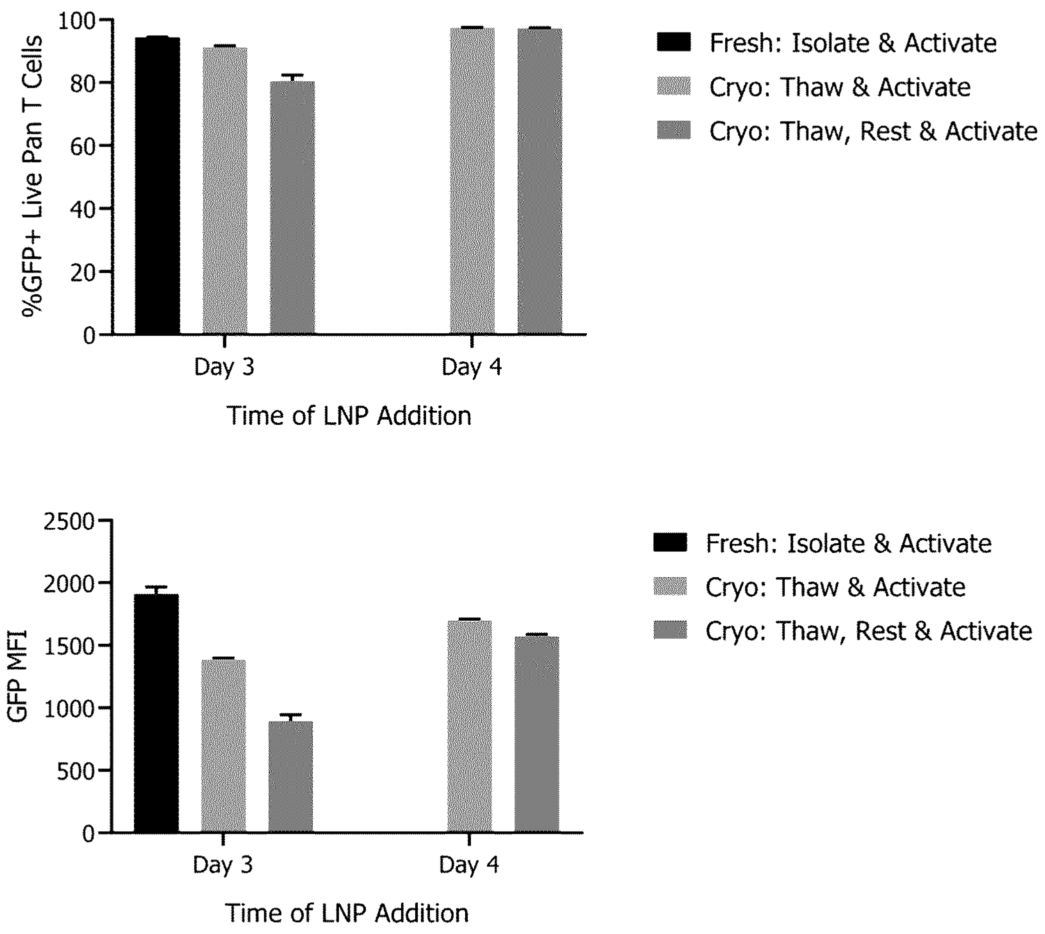
FIG. 16 is two bar graphs illustrating transfection efficiency and GFP expression in isolated primary human T cells mediated by mRNA-LNPs containing IL with CT10 composition at N/P 8 under five conditions, fresh T cells, frozen T cells treated on day three, and frozen T cells treated on day four, frozen T cells rested and treated on day 3, and frozen T cells rested and treated on day 4.

Effect of Cryopreservation on T Cell Transfectability with Compositions, and Optimization of Method GFP expression in isolated primary human T cells mediated by mRNA-LNPs containing BOCHD-C3-DMA with CT10 composition at N/P 8 is shown in FIG. 16. Transfection efficiency, viability and GFP MFI measured by flow cytometry 48 hours after LNP addition. T cells were isolated from whole blood using negative isolation procedure (EasySep™ Human T Cell Isolation Kit, Stemcell Technologies). A portion of the isolated T cells were immediately placed in Immunocult Human T Cell Expansion Media and activated using Immunocult™ Human CD3/CD28/CD2 Activator (Stemcell). For this portion of cells, 125 ng of mRNA encapsulated in LNPs was added 3 days after activation to 125,000 cells per well. Meanwhile, the other portion of isolated T cells were cryopreserved in liquid nitrogen. Cryopreserved T cells were thawed and either activated immediately or allowed to rest on ImmunoCult T Cell Expansion Media for 24 hours prior to activation using ImmunoCult™ Human CD3/CD28/CD2 Activator. T cells were dosed with mRNA-LNPs either 3 or 4 days after activation with 125 ng encapsulated mRNA per 125,000 cells. As shown in FIG. 16, there is no substantial diminishment in the efficiency of T Cell transfection post cryopreservation. There is an improvement by treating on day 4 as opposed to day 3 post activation in T cells that were previously cryopreserved.

Example 11

Effect of N/P Ratio

Figure 17:
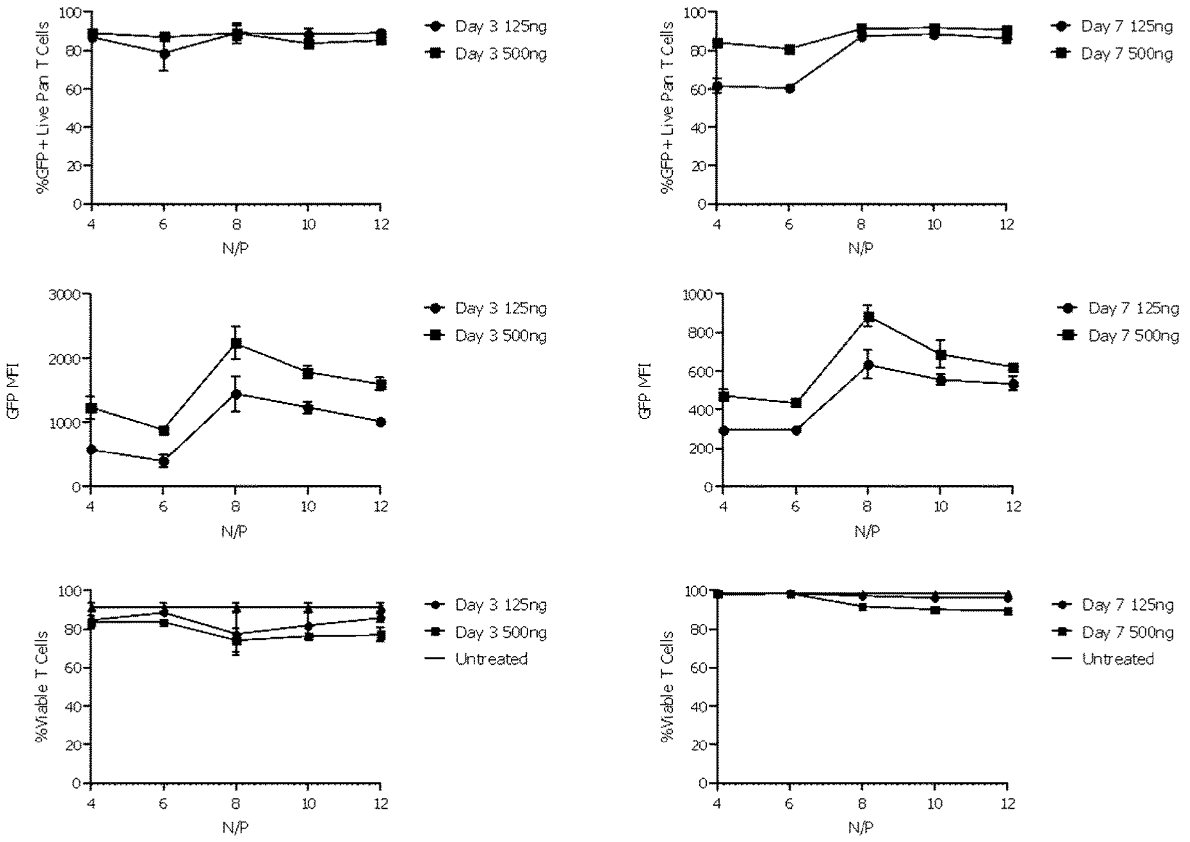
FIG. 17 is a series of line graphs showing GFP expression in isolated primary human T cells transfected with mRNA-LNPs containing BOCHD-C3-DMA as the IL, in a CT10 composition at N/P from 4-12. Transfection efficiency, viability and GFP MFI as measured by flow cytometry 48 hours after T cells were dosed with mRNA-LNPs either 3 days or 7 days after activation, with 125 ng or 500 ng of encapsulated mRNA per 125,000 cells.

Transfection efficiency, viability and GFP MFI were measured in isolated primary human T cells mediated by mRNA-LNPs containing BOCHD with CT10 composition at N/P 4-12, by flow cytometry 48 hours after LNP addition. Briefly; primary human T cells were isolated from fresh whole blood using a negative selection protocol and activated using a triple activator. T cells were dosed with mRNA-LNPs either 3 days or 7 days after activation with 125 ng or 500 ng of encapsulated m RNA per 125,000 cells. Results of the testing are shown in FIG. 17. The MFI increases in all cases in which N/P is 8 and higher. Transfection efficiency also increased at N/P 8 and higher.

Example 12

Dose Response and Duration of Expression

Figure 18:
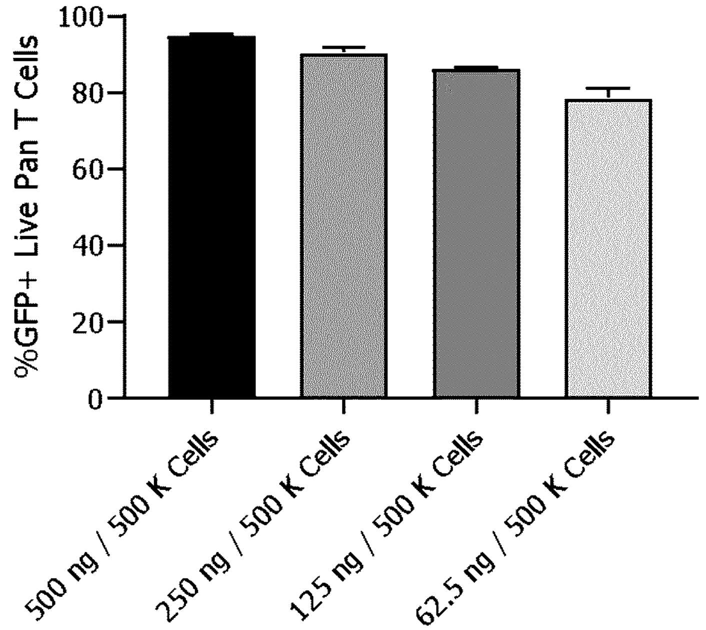
FIG. 18 is a graphical representation of GFP expression in isolated primary human T cells mediated by varying doses of mRNA-LNPs containing lipid BOCHD with CT1 0 composition at N/P 8, 3 days after activation of T cells.
Figure 18:
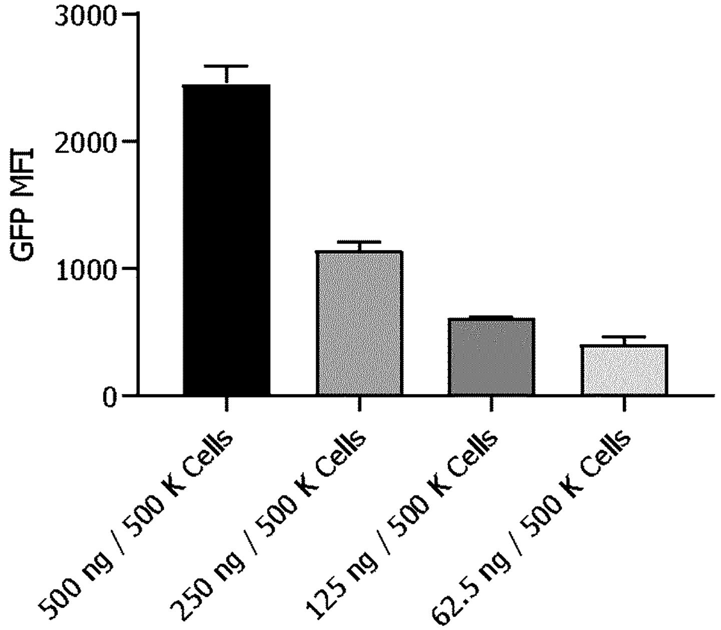

T Cells were isolated and activated using the triple activation protocol described in the Methods above. GFP expression mediated by varying doses of mRNA-LNPs exposed to T cells 3 days after activation is shown in FIG. 18. LNAPs contained BOCHD-C3-DMA as the ionizable lipid with CT10 composition, and mRNA was formulated at N/P 8. It was found that even the lowest dose of encapsulated mRNA tested, 62.5 ng mRNA per 500,000 cells, mediated efficient transfection with 80% GFP+ cells. Increasing the dose slightly increases the transfection efficiency, and greatly increases the GFP MFI. These results indicate that LNP-mediated transfection occurs evenly across the entire T cell population, and expression levels are easily titratable with volumetric addition of LNAPs.

Figure 19:
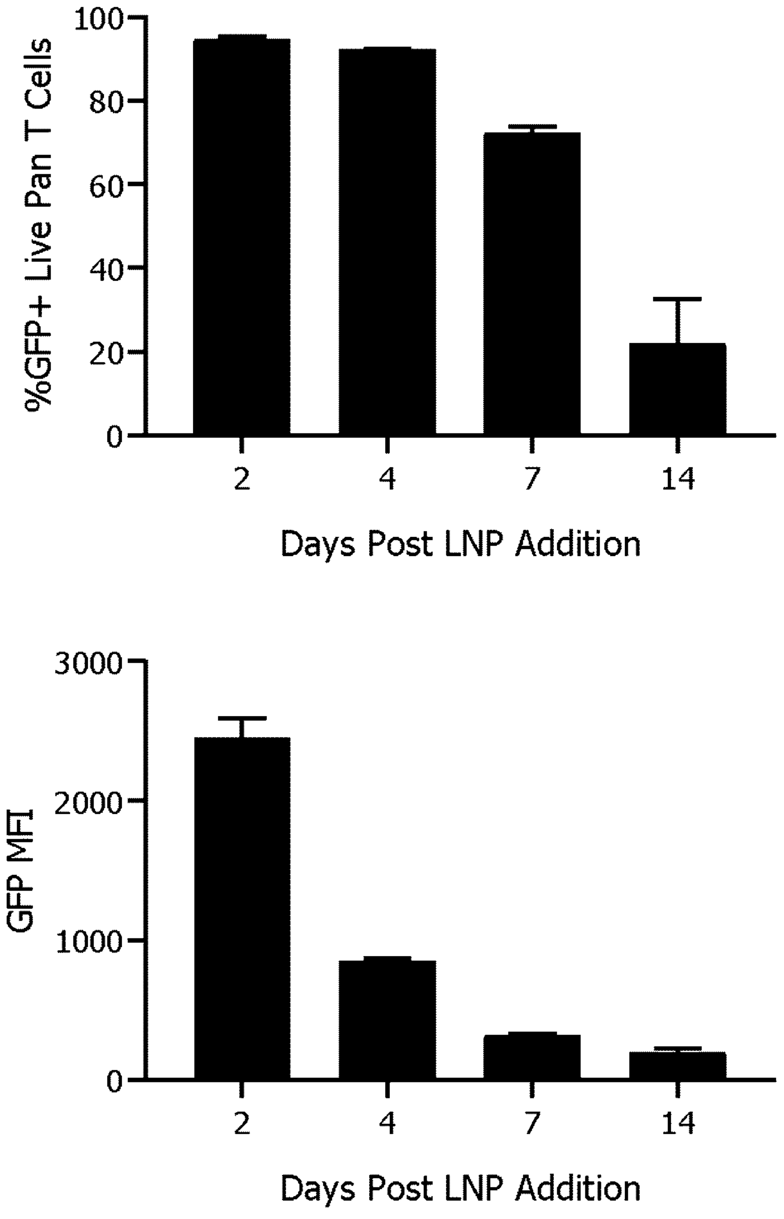
FIG. 19 is a set of bar graphs showing GFP % and GFP MFI of viable T cells measured by flow cytometry on days 2, 4, 7, or 14 post addition of CT10 LNAPs.

In a similar experiment as above, T cells were dosed with mRNA-LNPs and monitored for GFP expression for as long as 14 days after LNP addition. As seen in FIG. 19, the percent of GFP+ live Pan T cells was over 90% on days 2 and 4 post treatment. Even on day 14, there was some GFP being expressed.

Example 13

Erythropoietin mRNA Delivery and Expression

Figure 20:
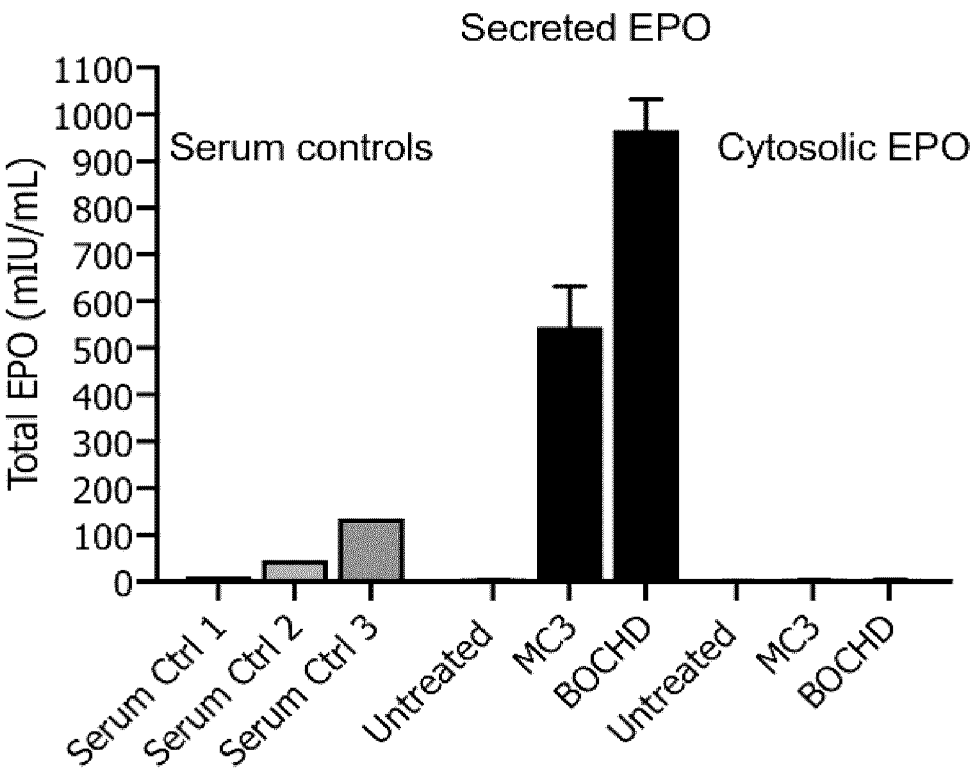
FIG. 20 is a bar graph showing total EPO expression in negatively selected T cells mediated by mRNA Lipid Nanoparticles (LNP) comprising CT10 lipid compositions, analyzed after 48 hours of treatment. The T cells were harvested and lysed for cytosolic EPO and media supernatant was sampled for secreted EPO. The ionizable lipid was BOCHD-C3-DMA or Dlin-MC3-DMA for the test compositions, and controls were untreated T cells and serum controls provided by the manufacturer of ELISA kit (Quantikine® IVD Human Epo ELISA, and Quantikine® Human Serum Controls)

The Quantikine® IVD Human Epo ELISA double-antibody sandwich assay was used to demonstrate mRNA delivery and activity in vitro. Reagents were acquired from Quantikine, Minneapolis, MN. The assay was performed as directed on the Quantikine® IVD® ELISA Human Erythropoietin Immunoassay protocol REF DEP00 Package Insert. Briefly; primary human T cells were isolated from fresh whole blood using a negative selection protocol and activated using a triple activator. At 7 days post-activation, the cells were treated with mRNA LNPs encoding EPO at 2 μg mRNA per 500,000 cells and N/P 10. After 48 hours of treatment with mRNA LNPs, the T cells were harvested and lysed for cytosolic EPO and media supernatant was sampled for secreted EPO. Quantikine® Human Serum Controls were used. The results are shown in FIG. 20 in mIU/mL.

Example 14

Figure 21:
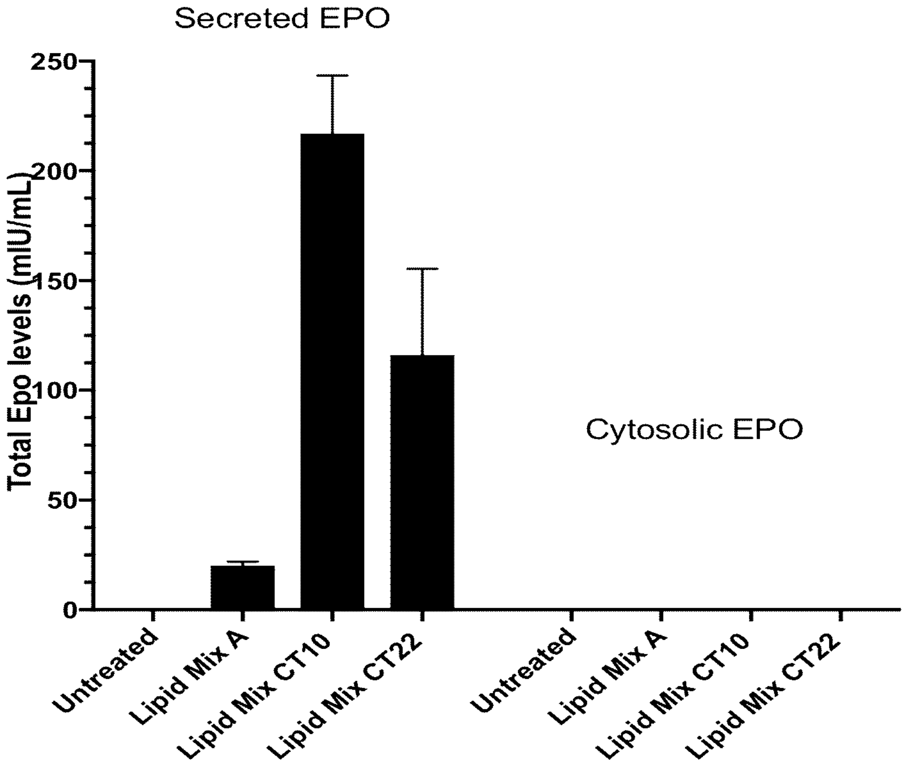
FIG. 21 is a bar graph showing total recombinant human erythropoietin (EPO) expression in negatively selected T cells mediated by mRNA LNP comprising CT10, CT22 and Lipid Mix A compositions, and analyzed after 48 h of treatment. The T cells were harvested and lysed for cytosolic EPO and media supernatant was sampled for secreted EPO. The ionizable lipid was BOCHD-C3-DMA for all three compositions.

Comparative Data of Lipid Mix Compositions Showing Activity with EPO mRNA LNPs in Primary Human T Cells Frozen human T cells, previously isolated from fresh human whole blood using a negative selection protocol, were thawed and activated using a triple activator as previously described. At seven days post-activation, T cells were dosed with CT10 formulated mRNA LNPs encoding recombinant human erythropoietin (EPO) determined by ELISA (R&D Systems) at 2 μg mRNA per 500,000 cells and N/P 10. After 48 hours of treatment with mRNA LNPs the T cells were harvested and lysed for cytosolic E PO and media supernatant was sampled for secreted EPO. Results are shown in FIG. 21. LNPs made with CT10 and CT22 compositions outperform lipid mix A composition LNP in this application. It was also found that LNPs made with BOCHD-C3-DMA resulted in a higher level of secreted EPO than MC3 LNPs did.

Example 15

Figure 22:
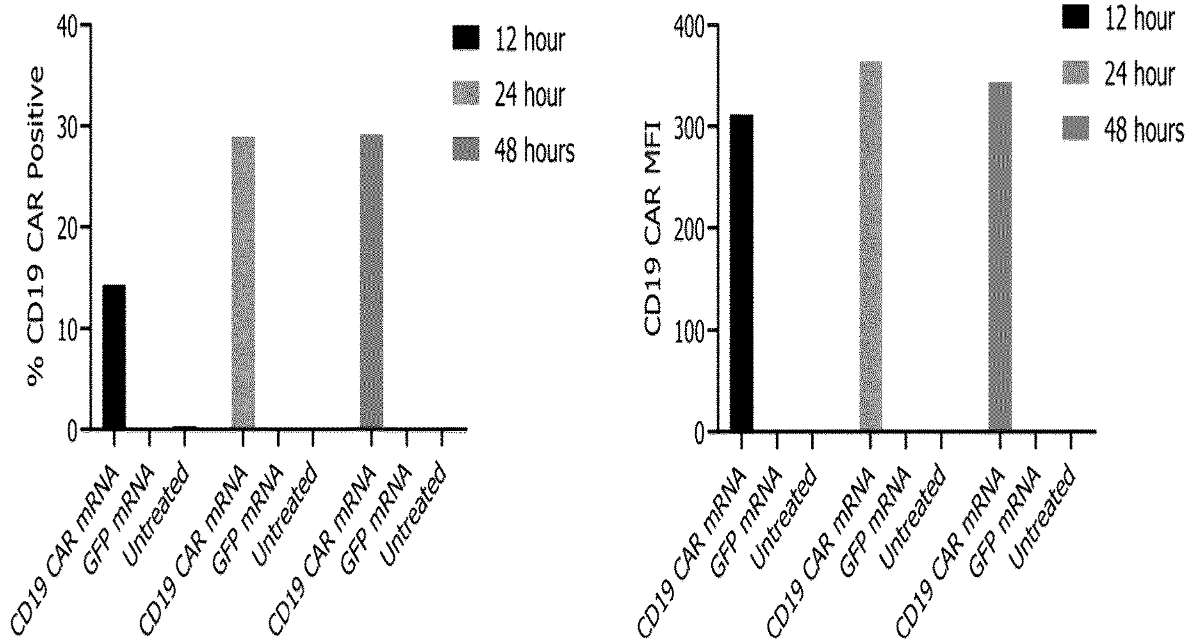
FIG. 22 is a graphical illustration of CD19 CAR expression in isolated primary human T cells mediated by mRNA-LNPs containing lipid BOCHD-C3-DMA with CT10 composition at N/P 8 showing transfection efficiency and MFI measured by flow cytometry 12, 24, and 48 hours after LNP addition 3 days after triple activation with 125 ng of encapsulated mRNA per 125,000 cells.

CD19 CAR expression in isolated primary human T cells mediated by mRNA-LNPs containing lipid BOCHD-C3-DMA with CT10 composition at N/P 8 was tested in vitro, with results shown in FIG. 22. Transfection efficiency and MFI were measured by flow cytometry 24 and 48 hours after LNP addition on day 3. T cells were isolated from whole blood using negative isolation procedure and T cell activation and expansion was carried out by triple activation in ImmunoCult™ Human T Cell Expansion Media. T cells were treated with 125 ng of encapsulated mRNA per 125,000 cells. As seen in FIG. 18, CD19 CAR expression was maintained over 48 hours in transfected T cells in vitro.

Example 16

Figure 23:
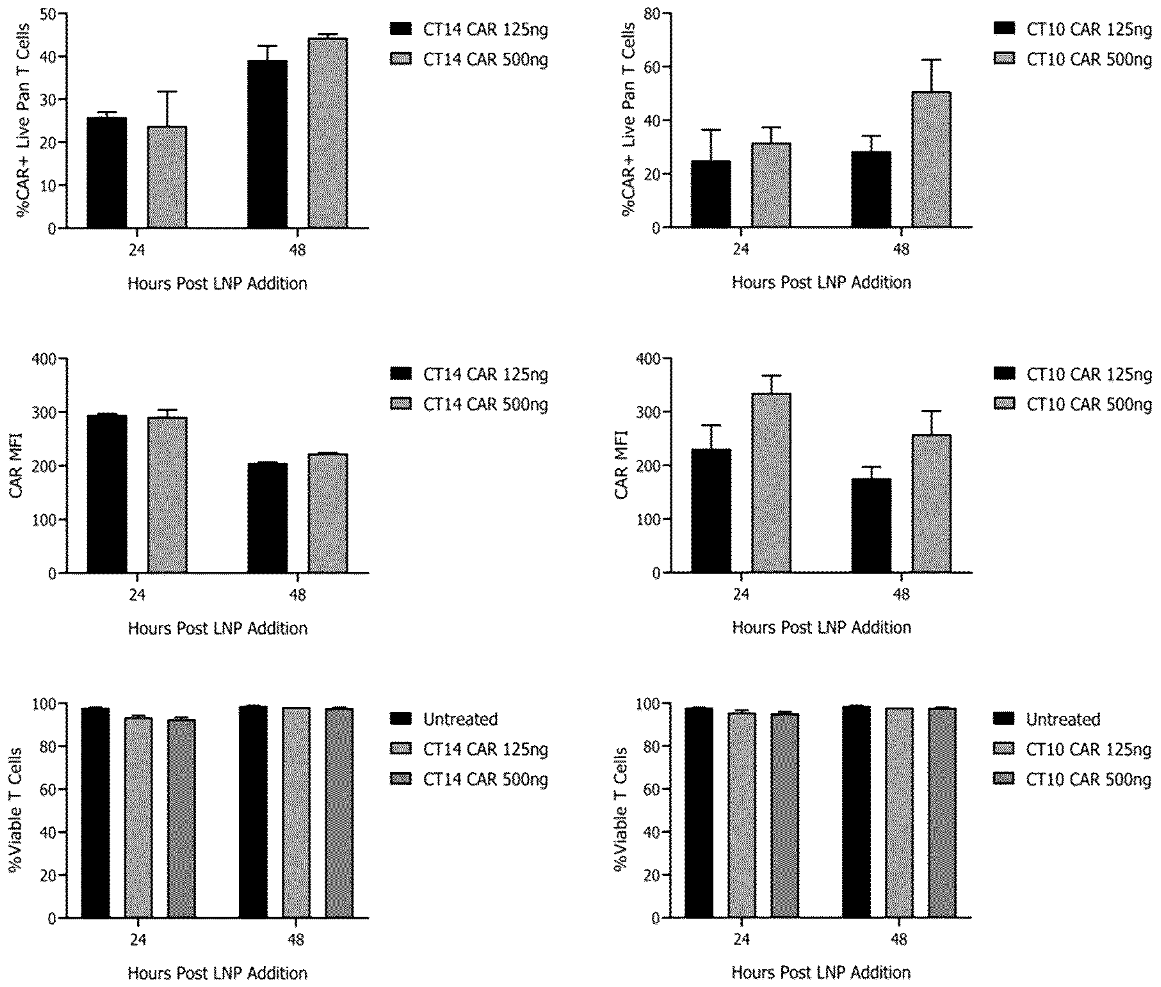
FIG. 23 is a series of bar graphs showing CD19 CAR expression in isolated primary human T cells mediated by mRNA-LNPs containing lipid BOCHD with CT10 or CT14 compositions at N/P 8. Transfection efficiency, MFIT cells were dosed with mRNA-LNPs 3 days after activation with 125 ng or 500 ng of encapsulated mRNA per 125, 000 cells.
Figure 24:
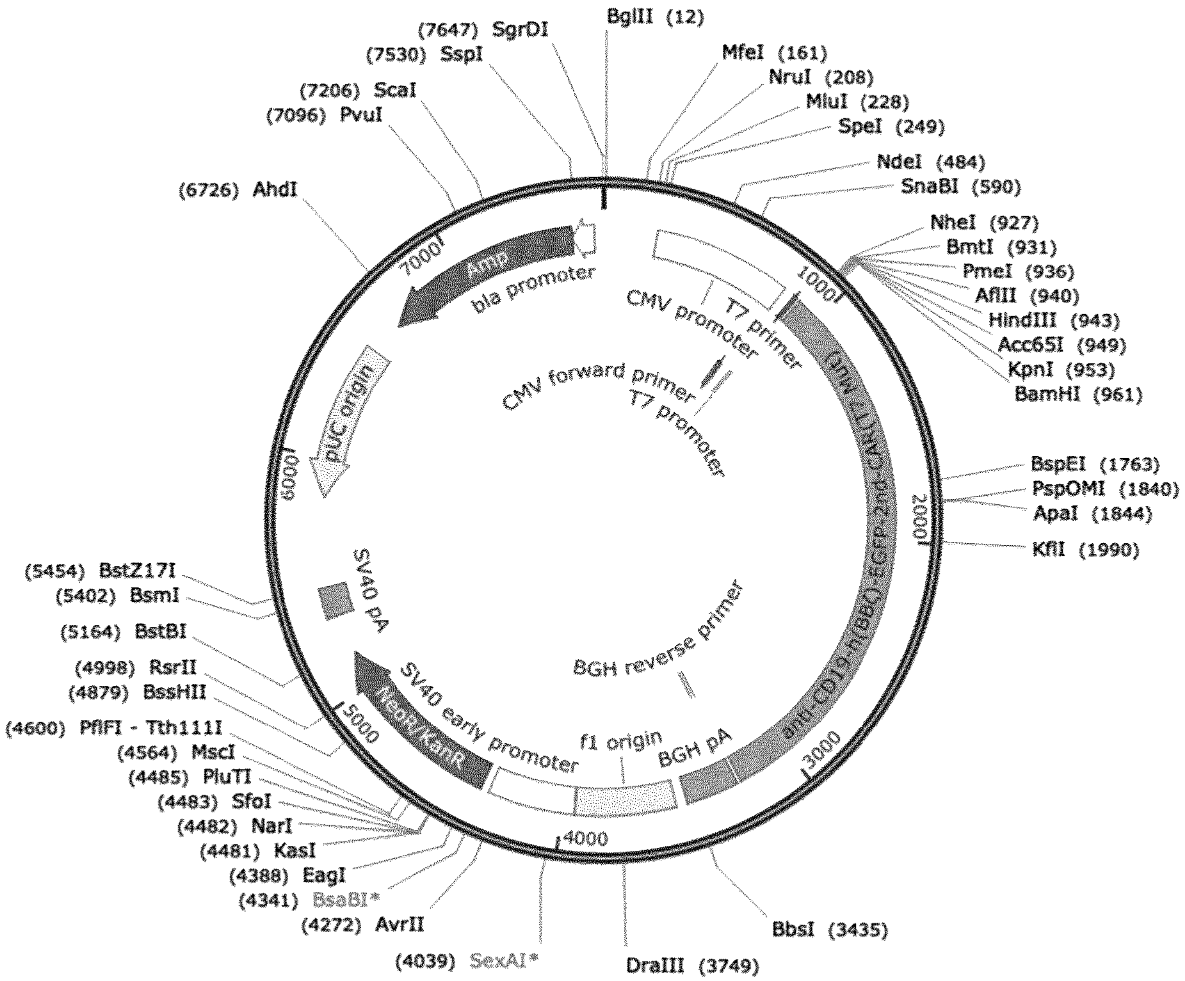
FIG. 24 is the genetic structure of the custom CAR plasmid showing the pcDNA3.1 cloning vector containing the anti-CD19-h(BB)-eGFP-2nd generation CAR (T7 Mut) gene cassette. The plasmid map was created using SnapGene® Viewer 4.1.9. This plasmid is linearized for in vitro transcription and capped to generate the custom mRNA encoding the anti-CD19-h(BB)-eGFP-2nd generation chimeric antigen receptor (CAR) expressed in human T cells.

CD19 CAR expression in isolated primary human T cells mediated by mRNA-LNPs containing lipid BOCHD with CT10 composition at N/P 8. The CAR vector pcDNA3.1 anti-CD19-h(BB Lambda)-EGFP-2nd-CAR (T7 Mut) 7661 bp was a commercial product on sale from Creative Biolabs, NY, USA. FIG. 23.

Transfection efficiency, MFI, and viability measured by flow cytometry 24 and 48 hours after LNP addition. T cells were isolated from whole blood using negative isolation and triple activator in ImmunoCult™ Human T Cell Expansion Media. T cells were dosed with mRNA-LNPs 3 days after activation with 125 ng or 500 ng of encapsulated mRNA per 125,000 cells in 250 ul Media. CT10 and CT14 compositions were tested. Data shown in FIG. 23 is from one donor, but similar results were seen in another donor in a different experiment.

While preferred embodiments have been described above and illustrated in the accompanying drawings, it will be evident to those skilled in the art that modifications may be made without departing from this disclosure. Such modifications are considered as possible variants comprised in the scope of the disclosure.

CITATIONS

1. Vairy, S.; Garcia, J. L.; Teira, P.; Bittencourt, H., CTL019 (tisagenlecleucel): CAR-T therapy for relapsed and refractory B-cell acute lymphoblastic leukemia. Drug design, development and therapy 2018, 12, 3885-3898.
2. Fitzgerald, J. C.; Weiss, S. L.; Maude, S. L.; Barrett, D. M.; Lacey, S. F.; Melenhorst, J. J.; Shaw, P.; Berg, R. A.; June, C. H.; Porter, D. L.; Frey, N. V.; Grupp, S. A.; Teachey, D. T., Cytokine Release Syndrome After Chimeric Antigen Receptor T Cell Therapy for Acute Lymphoblastic Leukemia. Crit Care Med 2017, 45 (2), e124-e131.
3. Frey, N.; Porter, D., Cytokine Release Syndrome with Chimeric Antigen Receptor T Cell Therapy. Biol Blood Marrow Transplant 2018.
4. Porter, D. L.; Hwang, W. T.; Frey, N. V.; Lacey, S. F.; Shaw, P. A.; Loren, A. W.; Bagg, A.; Marcucci, K. T.; Shen, A.; Gonzalez, V.; Ambrose, D.; Grupp, S. A.; Chew, A.; Zheng, Z.; Milone, M. C.; Levine, B. L.; Melenhorst, J. J.; June, C. H., Chimeric antigen receptor T cells persist and induce sustained remissions in relapsed refractory chronic lymphocytic leukemia. Sci Transl Med 2015, 7 (303), 303ra139.
5. Monjezi, R.; Miskey, C.; Gogishvili, T.; Schleef, M.; Schmeer, M.; Einsele, H.; Ivies, Z.; Hudecek, M., Enhanced CAR T-cell engineering using non-viral Sleeping Beauty transposition from minicircle vectors. Leukemia 2017, 31 (1), 186-194.
6. Patel, S.; Ashwanikumar, N.; Robinson, E.; Xia, Y.; Mihai, C.; Griffith, J. P.; Hou, S.; Esposito, A. A.; Ketova, T.; Welsher, K.; Joyal, J. L.; Almarsson, b.; Sahay, G., Naturally-occurring cholesterol analogues in lipid nanoparticles induce polymorphic shape and enhance intracellular delivery of mRNA. Nature Communications 2020, 11 (1), 983.
7. Garg, S.; Heuck, G.; Ip, S.; Ramsay, E., Microfluidics: a transformational tool for nanomedicine development and production. J Drug Target 2016, 24 (9), 821-835.
8. Zhang, S.-h.; Shen, S.-c.; Chen, Z.; Yun, J.-x.; Yao, K.-j.; Chen, B.-b.; Chen, J.-z., Preparation of solid lipid nanoparticles in co-flowing microchannels. Chemical Engineering Journal 2008, 144 (2), 324-328.
9. Stroock, A. D.; Dertinger, S. K.; Ajdari, A.; Mezic, I.; Stone, H. A.; Whitesides, G. M., Chaotic mixer for microchannels. Science 2002, 295 (5555), 647-51.
10. JEFFS, L. B., et al., A Scalable, Extrusion-Free Method for Efficient Liposomal Encapsulation of Plasmid DNA. Pharmaceutical Research 2005, 22 (3), 362-372.
11. Nianias, A.; Themeli, M., Induced Pluripotent Stem Cell (iPSC)-Derived Lymphocytes for Adoptive Cell Immunotherapy: Recent Advances and Challenges. Current hematologic malignancy reports 2019, 14 (4), 261-268.

12. Iriguchi, S.; Kaneko, S., Toward the development of true "off-the-shelf" synthetic T-cell immunotherapy. Cancer science 2019, 110 (1), 16-22.

We claim:

1. A lipid mix composition for forming lipid particles in association with a nucleic acid, for use in transfecting the nucleic acid into T cells, the composition comprising:

about 40-50 Mol % ionizable lipid, about 10-20 Mol % a structural lipid, wherein the structural lipid comprises distearoylphosphatidylcholine (DSPC), about 35 to 40 Mol % sterol, and about 0.1-3 Mol % stabilizer, wherein the stabilizer comprises polyoxyethylene (10) stearyl ether, D-α-Tocopherol polyethylene glycol 1000 succinate (TPGS), or combinations thereof.

2. The lipid mix composition of claim 1, wherein said transfecting takes place ex vivo or in vitro.

3. The lipid mix composition of claim 1, wherein the ionizable lipid is an aminolipid.

4. The lipid mix composition of claim 3, wherein the aminolipid is selected from the group consisting of BOCHD-C3-DMA, Dlin-MC3-DMA, DODMA, and DLin-KC2-DMA.

5. The lipid mix composition of claim 1, wherein the ionizable lipid is C12-200.

6. The lipid mix composition of claim 1, wherein the ionizable lipid is about 40 Mol %, the structural lipid is about 20 Mol % DSPC, the sterol is from 37-40 Mol %, and the stabilizer is from 0.5 Mol % to 2.5 Mol %.

7. The lipid mix composition of claim 1, wherein the ionizable lipid is about 50 Mol %, the structural lipid is about 10 Mol % DSPC, the sterol is from 37-40 Mol %, and the stabilizer is about 0.5 Mol % to 2.5 Mol %.

8. The lipid mix composition of claim 1, wherein an N/P ratio is from 4-12.

9. The lipid mix composition of claim 8, wherein the N/P ratio is from 8-10.

10. The lipid mix composition of claim 6, wherein the stabilizer is 0.5 Mol % TPGS, 2.5 Mol % TPGS, or 2.5 Mol % polyoxyethylene (10) stearyl ether.

11. The lipid mix composition of claim 7, wherein the stabilizer is 0.5 Mol % TPGS, 2.5 Mol % TPGS, or 2.5 Mol % polyoxyethylene (10) stearyl ether.

* * * * *